(12) United States Patent
Yonekawa et al.

(10) Patent No.: US 11,795,446 B2
(45) Date of Patent: Oct. 24, 2023

(54) CARRIER AND TESTING METHOD

(71) Applicant: RICOH COMPANY, LTD., Tokyo (JP)

(72) Inventors: Yuuki Yonekawa, Sagamihara (JP); Hirotaka Unno, Yokohama (JP); Satoshi Nakazawa, Yokohama (JP)

(73) Assignee: Ricoh Company, Ltd., Tokyo (JP)

(*) Notice: Subject to any disclaimer, the term of this patent is extended or adjusted under 35 U.S.C. 154(b) by 291 days.

(21) Appl. No.: 17/203,615

(22) Filed: Mar. 16, 2021

(65) Prior Publication Data

US 2021/0292739 A1    Sep. 23, 2021

(30) Foreign Application Priority Data

Mar. 23, 2020  (JP) .................. 2020-051158

(51) Int. Cl.
  *C12N 11/12*   (2006.01)
  *C12Q 1/6806*  (2018.01)
  *C12Q 1/686*   (2018.01)

(52) U.S. Cl.
  CPC .............. *C12N 11/12* (2013.01); *C12Q 1/686* (2013.01); *C12Q 1/6806* (2013.01)

(58) Field of Classification Search
  CPC .................................................. C12Q 1/6806
  See application file for complete search history.

(56) References Cited

U.S. PATENT DOCUMENTS

| | | |
|---|---|---|
| 2005/0032192 A1 | 2/2005 | Vesey et al. |
| 2012/0289690 A1 | 11/2012 | Page |
| 2019/0151843 A1 | 5/2019 | Kawashima et al. |
| 2019/0284611 A1 | 9/2019 | Kawashima et al. |
| 2020/0194100 A1 | 6/2020 | Osaki et al. |
| 2020/0384464 A1 | 12/2020 | Kawashima et al. |
| 2020/0384664 A1 | 12/2020 | Kawashima et al. |
| 2021/0010072 A1 | 1/2021 | Suzuki et al. |

FOREIGN PATENT DOCUMENTS

| | | |
|---|---|---|
| EP | 3712242 | 9/2020 |
| JP | 4414220 | 2/2010 |
| JP | 5164050 | 3/2013 |
| JP | 5875230 | 3/2016 |
| JP | 85875230 | 3/2016 |
| JP | 5899118 | 4/2016 |
| JP | 2019-088268 | 6/2019 |
| JP | 2019/092494 | 6/2019 |
| JP | 2019-162101 | 9/2019 |
| JP | 2019-216703 | 12/2019 |
| JP | 2019-216704 | 12/2019 |
| JP | 2020-054327 | 4/2020 |
| JP | 2020-096578 | 6/2020 |
| JP | 2020-108358 | 7/2020 |
| JP | 2019-092495 | 6/2021 |
| WO | 01/51601 | 7/2001 |
| WO | 2018025856 | 2/2018 |
| WO | 2019/093528 | 5/2019 |

OTHER PUBLICATIONS

Peluso, A.L. et al., Use of FTA CArds for the Storage of Breast Carcinoma Nucleic Acid on Fine-Needle Aspiration Samples, Cancer Cytopathol., vol. 123, pp. 582-592 (Year: 2015).*
U.S. Appl. No. 16/763,161, filed May 11, 2020 (of record).
U.S. Appl. No. 16/766,117, filed May 21, 2020 (of record).
Extended European Search Report dated Aug. 17, 2021 in European Application 21162246.9, 7 pages.
Moon et al. "Drop-on-Demand Single Cell Isolation and Total RNA Analysis", PLOS ONE, vol. 6, Issue 3, Mar. 2011, pp. 1-10.

\* cited by examiner

*Primary Examiner* — Teresa E Strzelecka
(74) *Attorney, Agent, or Firm* — Grüneberg and Myers PLLC

(57) ABSTRACT

A carrier includes a supporting part on which a specific number of cells A are supported. The cells A contain a specific number of copies of a nucleic acid, and the supporting part is made of a water-decomposable material.

16 Claims, 20 Drawing Sheets

Specification includes a Sequence Listing.

CARRIER AND TESTING METHOD

BACKGROUND OF THE INVENTION

Field of the Invention

The present invention relates to a carrier and a testing method. Specifically, the present invention provides a carrier and a method for testing the accuracy of a measurement value of a detection target gene in a cell sample, where the measurement value is obtained from a genetic testing apparatus.

Priority is claimed on Japanese Patent Application No. 2020-051158, filed on Mar. 23, 2020, the content of which is incorporated herein by reference.

Description of Related Art

In the fields of food, environmental testing, and medical treatments, a genetic test that detects and measures a nucleic acid has been performed. In recent years, the sensitivity of analytical technology has increased, and it has become possible to measure a measurement target nucleic acid in units of copy number. As the measurement target nucleic acid, a nucleic acid that is extracted from food, environmental water, blood, urine, tissue, or the like as a measurement target, has been used.

For the extraction of nucleic acid, a method in which the nucleic acid is captured by a column or magnetic beads and washed to remove impurities and the like, and then the nucleic acid is eluted has been used.

As the method for measuring the copy number of the measurement target nucleic acid, real-time PCR or digital PCR, which applies amplification by a polymerase chain reaction (PCR), has been used. Real-time PCR is a method for measuring amplification by PCR in real time and measures the amount of amplification of a DNA sequence of a target nucleic acid using fluorescent dyes. It is possible to quantify the copy number of the nucleic acid by using a dilution series of the nucleic acid such as plasmid DNA, the copy number of which is known.

However, in the conventional genetic tests, the copy number of the target nucleic acid is quantified by real-time PCR in a state where the extraction efficiency of the nucleic acid is unknown, and thus there is a problem in that the accurate copy number of the target nucleic acid contained in the actual sample (food, environmental water, blood, urine, tissue, or the like) is not known.

In the extraction of nucleic acid, since the extraction efficiency differs depending on the extraction method, the base sequence of the nucleic acid, the kind of extraction target sample, or the like, there is a method of performing extraction in a state where an internal standard is added as a reference for each work. However, there remains a problem in that since the plasmid DNA used as an internal standard is not covered with a cell membrane or the like, the extraction conditions are different from those of the target sample, and since a micropipette or the like is used when adding the internal standard, the copy number of the internal standard varies greatly, even in the case where actual application is possible.

In addition, in the case where a sample similar to the actual sample is used as an internal standard, it is not desirable to manipulate substances that affect the body, such as cancer cells and viruses.

Patent Document 1 discloses a method for detecting a specific gene contained in a test sample such as a biological sample, a clinical sample, or food, which includes bringing a water-decomposable carrier supporting the test sample into contact with a reaction solution containing a buffer, a DNA polymerase, and a primer, and detecting whether or not the specific gene is contained in the reaction solution using optical means. According to the method disclosed in Patent Document 1, a gene contained in the test sample can be amplified without the need for pretreatment such as separation or purification of the nucleic acid contained in the test sample, and the specific gene contained in the test sample can be detected with high sensitivity.

However, since there are no internal standards in the method disclosed in Patent Document 1, the extraction efficiency of a nucleic acid from the extraction target test sample remains unknown, and it is not possible to know the accurate copy number of the detected gene.

SUMMARY OF THE INVENTION

The present invention provides a novel carrier that provides accurate extraction efficiency of a nucleic acid.

A carrier includes a supporting part on which a specific number of cells A are supported, the cells A contain a specific number of copies of nucleic acid, and the supporting part is made of a water-decomposable material.

According to the carrier of the above aspect, it is possible to provide a carrier with which accurate extraction efficiency of nucleic acid is obtained.

BRIEF DESCRIPTION OF THE DRAWINGS

FIG. 6 (b) is a schematic view showing another example of a voltage applied to a piezoelectric element.

DETAILED DESCRIPTION OF THE INVENTION

Figure 1:
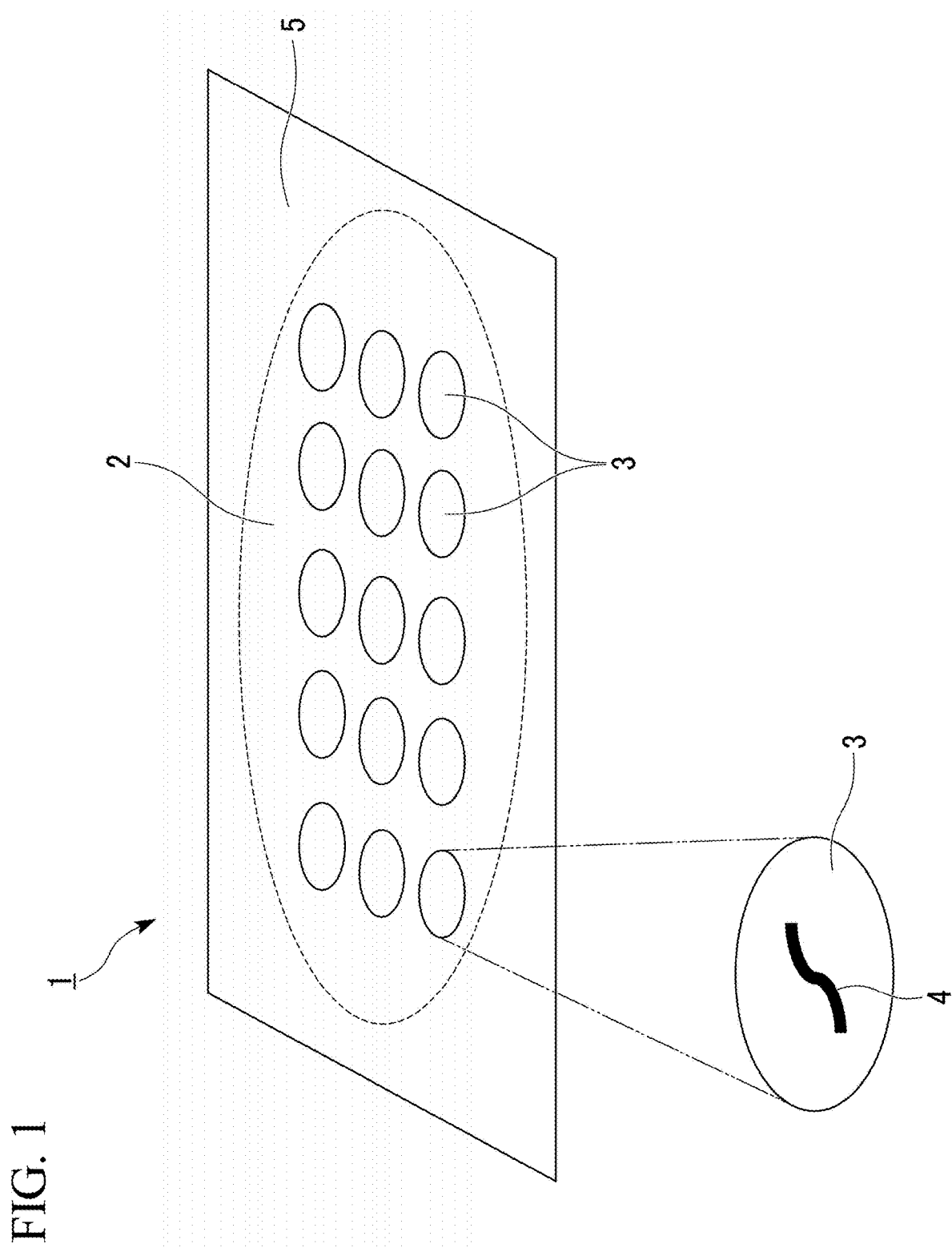
FIG. 1 is a view showing a carrier according to one embodiment of the present invention.

Hereinafter, a carrier and a testing method according to one embodiment of the present invention (hereinafter, may be simply referred to as a "carrier of the present embodiment" and a "testing method of the present embodiment", respectively) will be described with reference to the specific embodiments and drawings, as necessary. Such embodiments and drawings are merely examples for facilitating the understanding of the present invention and do not limit the present invention. That is, the shapes, dimensions, arrangements, or the like of the members described below can be changed and improved without departing from the gist of the present invention, and the present invention includes equivalents thereof.

Further, in all the drawings, the same constitutional elements are designated by the same reference numeral, and the description will not be duplicated.

In the present specification, all technical and scientific terms used in the present specification have the same meaning as those commonly understood by the persons skilled in the art, unless defined otherwise. All patents, applications, and other publications and information referred to in the present specification are incorporated herein by reference in their entirety. In addition, in the case where there is a conflict between the publication referenced in the present specification and the description in the present specification, the description in the present specification will prevail.

<Carrier>

FIG. 1 is a view showing a carrier according to one embodiment of the present invention.

A carrier 1 is composed of a base material 5 having a supporting part 2 on which a specific number of cells A (3) are supported. The cell A (3) contains a specific number of copies of a nucleic acid 4. The supporting part 2 is made of a water-decomposable material.

As described in the background technique described above, a measurement value obtained from a genetic testing apparatus is affected by the extraction efficiency of a gene, but the extraction efficiency of a gene has not been known so far. On the other hand, in the case where the carrier of the present embodiment is used, the extraction efficiency of a gene can be calculated as described later. Accordingly, the carrier of the present embodiment can be said to be a carrier for testing the accuracy of a measurement value of a detection target gene in a cell sample, where the measurement value is obtained from a genetic testing apparatus. The accuracy of a measurement value of a detection target gene in a cell sample, where the measurement value is obtained from a genetic testing apparatus, includes, for example, the accuracy of the extraction efficiency of the detection target gene in the cell sample.

In the present specification, examples of the "genetic testing apparatus" include a quantitative PCR apparatus, a qualitative PCR apparatus, and a nucleic acid sequencing apparatus (particularly, a next generation sequencer (NGS)). The next generation sequencer is a group of base sequence analyzers that have been developed in recent years and have greatly improved the analytical capabilities since a large number of clonally amplified DNA templates or single DNA molecules are subjected to parallel processing treatment in a flow cell.

Among these, the genetic testing apparatus is preferably a quantitative PCR apparatus.

The quantification value (quantitative copy number) of the detection target gene, which is calculated by a quantitative PCR apparatus, can be expressed by the following expression and is affected by the extraction efficiency and amplification efficiency of a gene.

(Quantitative copy number)=[copy number of gene present in cell sample]×(extraction efficiency)× (amplification efficiency)

Therefore, the accuracy of a quantification value of a detection target gene in a cell sample, where the quantification value is obtained from the quantitative PCR apparatus, includes, for example, the accuracy of the extraction efficiency of the detection target gene from the cell sample and the accuracy of the amplification efficiency of the detection target gene.

The amplification efficiency can be calculated from the calibration curve created by the quantitative PCR apparatus. On the other hand, in the case where an internal standard is used, the extraction efficiency can be checked.

However, in the conventional method, in the case where a nucleic acid was used as an internal standard for the purpose of checking the extraction efficiency of a nucleic acid, it was common to dilute the nucleic acid and apply the diluted nucleic acid using a micropipette or the like. In this method, the copy number of the applied nucleic acid was not accurate due to the variation derived from dilution and dispensing. In addition, since the nucleic acid contained in the cell was not used, the extraction efficiency of the nucleic acid from the cell could not be determined.

On the other hand, in the carrier 1, the number of cells A (3) is the specific number of cells which are accurately counted, each of the cells A (3) contains a specific number of copies of the nucleic acid 4, and the supporting part 2 on which the cells A (3) are supported is made of a water-decomposable material. Therefore, in the case where the carrier 1 is added to an aqueous solution, the supporting part 2 made of a water-decomposable material is dissolved or dispersed, and a specific number of the cells A (3) supported by the carrier are all dispersed in the aqueous solution. As a result, as shown in Examples described later, in the case where the carrier 1 is used, there is no variation due to dilution and dispensing, and the extraction efficiency of the nucleic acid 4 from the cells A (3) can be accurately determined. Accordingly, the carrier of the present embodiment can be also said to be a carrier for calculating the extraction efficiency of a detection target gene in a cell sample.

Further, in the case where the carrier 1 is used as an internal standard for the quantification of a detection target gene in a cell sample by a quantitative PCR apparatus, the extraction efficiency of the nucleic acid 4 from the cells A (3) of the carrier 1 can be accurately assessed. Furthermore, in the case where a calibration curve is created by using a plurality of the carriers 1 which are different in the total copy number of the nucleic acids 4 present on the base material, the amplification efficiency of the nucleic acid 4 can be accurately assessed. As a result, in the case where these extraction efficiency and amplification efficiency calculated using the carrier of the present embodiment are substituted into the above-described expression which represents a quantitative copy number of a detection target gene, the amount of the detection target gene actually present in the cell sample can be estimated. That is, in the case where the carrier of the present embodiment is used, the detection target gene in the cell sample can be accurately quantified. Accordingly, the carrier of the present embodiment can be also said to be a carrier for accurately quantifying a detection target gene in a cell sample.

The cell sample may be a sample containing cells containing a detection target gene, and specific examples thereof include various liquids such as body fluid and a cell suspension. Examples of the body fluid include whole blood, serum, plasma, urine, semen, breast milk, sweat, interstitial fluid, interstitial lymph, bone marrow fluid, tissue fluid, saliva, gastric fluid, joint fluid, pleural effusion, bile, ascites, and amniotic fluid.

The detection target gene may be DNA or RNA, and examples thereof include a species-specific sequence and a genetic polymorphism (for example, a single nucleotide polymorphism (SNP)).

The length of the detection target gene is not particularly limited and may be, for example, 20 bases or more and several hundred thousand bases or less.

Examples of the quantitative PCR (Q-PCR) include real-time PCR and digital PCR.

Real-time PCR quantifies a template nucleic acid based on the amplification rate by measuring the amplification by PCR over time (in real time). Quantification is performed using a fluorescent dye, and the quantification using a fluorescence dye includes mainly an intercalation method and a hybridization method.

In the intercalation method, a template nucleic acid is amplified in the presence of an intercalator that is specifically inserted (intercalates) into double-stranded DNA to emit fluorescence. Examples of the intercalator include SYBR Green I (CAS number: 163795-75-3) or a derivative thereof. On the other hand, in the hybridization method, a method using a TaqMan (registered trade mark) probe is the most common, and a probe in which a fluorescent substance and a quenching substance are bonded to an oligonucleotide complementary to the target nucleic acid sequence is used.

In the digital PCR, a sample DNA diluted to the limit (diluted so that the target DNA becomes 1 or 0 in each micro-compartment) is dispersed in a micro-compartment, PCR amplification is performed, and the presence or absence of an amplification product is detected in each micro-compartment, thereby quantifying the absolute quantity of the copy number.

[Supporting Part]

The supporting part 2 is made of a water-decomposable material. The term "water-decomposable" as used herein means the property of being dissolved or dispersed in water. The water-decomposable material is not particularly limited, and may be dissolved or dispersed in the cold water of 0° C. or higher and 10° C. or lower or water at room temperature of 25° C.±5° C. without heating or may be dissolved or dispersed in hot water of about 50° C. or higher and 100° C. or lower.

Examples of the water-decomposable material include water-decomposable paper and water-decomposable film. Examples of the commercially available water-decomposable material include Clair (dissolved or dispersed with the heat of 80° C. or higher), Clair 50 (dissolved or dispersed with the heat of 50° C. or higher), and Clair 100 (dissolved or dispersed with cold water) manufactured by Ina Food Industry Co., Ltd.); and a water-soluble paper MDP (for example, 120 MDP) and a water-soluble paper CD-2, manufactured by Nippon Paper Papylia Co., Ltd.

The size of the supporting part 2 is not particularly limited, and can be appropriately set depending on the reaction space for extracting and detecting a nucleic acid and the amount of the reaction solution. For example, in the case of performing dissolution or dispersion in an aqueous solution of about 100 μL, the supporting part 2 preferably has a circular shape having a diameter of about 1 mm or more and 6 mm or less.

In the present specification, the term "supporting" means a state in which cells A (3) are indirectly or directly attached to the supporting part 2.

In the carrier of the present embodiment, the number of cells A (3) supported on the supporting part 2 is specified, and the copy number of the nucleic acid 4 contained in the cell A (3) is specified. That is, the copy number of the nucleic acid 4 which is present on the carrier 1 is specified. As a result, the copy numbers of the nucleic acid 4 before and after extraction can be compared, and the extraction efficiency of the nucleic acid 4 from the cells can be calculated.

[Specific Number of Cells]

In the present specification, the description that the number of cells A supported on the supporting part is specified means that the number of cells A supported on the supporting part is specified with a predetermined degree of accuracy or higher. That is, the number of cells A actually supported on the supporting part is known. That is, the specific number of cells in the present specification is more accurate and reliable as the numerical number than the number of cells (an estimated value by calculation) as determined by conventional serial dilution, and in particular, is a controlled value regardless of the Poisson distribution even in the fewer cell range of 1,000 cells or fewer.

For the controlled value, in general, the coefficient of variation CV, which represents uncertainty, is preferably within the value of either $CV<1/\sqrt{x}$ with respect to the average number of molecules x or $CV \leq 20\%$.

The number of cells A is not particularly limited, but is preferably 1 or more and 500 or less, more preferably 1 or more and 200 or less, still more preferably 1 or more and 100 or less, and particularly preferably 1 or more and 50 or less.

[Specific Copy Number]

In the present specification, the description that the copy number of the nucleic acid contained in the cell A is specified means that the number of nucleic acids contained in the cell A is specified with a predetermined degree of accuracy or higher. That is, the number of nucleic acids contained in the cell actually supported on the supporting part are known.

Further, in the present specification, the description that the copy number of the nucleic acid present on the base material is specified means that the number of nucleic acids present on the base material is specified with a predetermined degree of accuracy or higher. That is, the number of nucleic acids actually present on the base material are known.

That is, the specific copy number in the present specification is more accurate and reliable as the numerical number than the copy number (an estimated value by calculation) as determined by conventional serial dilution, and in particular, is a controlled value regardless of the Poisson distribution even in the fewer copy number range of 1,000 copies or fewer.

For the controlled value, in general, the coefficient of variation CV, which represents uncertainty, is preferably within the value of either $CV<1/\sqrt{x}$ with respect to the average number of molecules x or $CV \leq 20\%$.

Here, the "copy number" of the acid and the "number of molecules" of the nucleic acid may be associated with each other. Specifically, for example, in the case of a G1 phase yeast in which a base sequence of a nucleic acid is introduced into two places on the genome, in the case where the number of yeasts is 1, the number of molecules of the nucleic acid (the number of the identical chromosome) is 1, and the copy number of the nucleic acid is 2. In the present specification, the specific copy number of the nucleic acid may be referred to as the absolute number of the nucleic acid.

In extracting a nucleic acid from the cell A supported on the supporting part using the carrier of the present embodiment, in the case where there are a plurality of reaction spaces (hereinafter, may be referred to as "wells") containing the carrier, the description that the same copy number of the nucleic acid is contained in each well means that the scattering of the number of nucleic acids, which occurs in the case where the reaction spaces are filled with the carriers, is within the allowable range. Whether or not the scattering of the numbers of nucleic acids is within the allowable range can be determined based on the information on uncertainty described below.

Examples of the information on the specific copy number of the nucleic acid include the information on uncertainty and the information on the nucleic acid.

ISO/IEC Guide 99: 2007 [International Metrology Term—Basic and General Concept and Related Term (VIM)] defines that "uncertainty" is a "parameter that characterizes the scattering of values that accompany a measurement result and can be reasonably linked to a measured quantity".

Here, "a value that can be reasonably linked to a measured quantity" means a candidate for a true value of the measured quantity. That is, the uncertainty means information on the scattering of measurement results, which is derived from operations involved in the manufacture of the measurement target, equipment, or the like. The greater the uncertainty is, the greater the scattering to be expected in the measurement result is. The uncertainty may be, for example, a standard deviation obtained from the measurement result, or a half value of the confidence level indicated as the range of values in which the true value is included with at least a predetermined probability.

The uncertainty can be calculated based on Guide to the Expression of Uncertainty in Measurement (GUM: ISO/IEC Guide 98-3); Japan Accreditation Board Note 10, Guideline for measurement uncertainty in test; or the like.

As a method for calculating the uncertainty, for example, two methods of a type A evaluation method using statistics of measurement values and the like, and a type B evaluation method using the information on uncertainty obtained from a calibration certificate, a manufacturer's specification, published information, or the like can be applied.

The uncertainties can be expressed at the same confidence level by converting all the uncertainties obtained from factors such as operation and measurement into standard uncertainties. The standard uncertainty indicates the scattering of the average value obtained from the measurement values.

In one example of the method for calculating the uncertainty, for example, factors that cause uncertainties are extracted and the uncertainty (the standard deviation) of each of the factors is calculated. Subsequently, the calculated uncertainty of each of the factors is synthesized by the sum-of-squares method to calculate a synthetic standard uncertainty. Since the sum-of-squares method is used in the calculation of the synthetic standard uncertainty, among the factors that cause uncertainties, a factor providing an uncertainty that is sufficiently small can be ignored.

As the information on uncertainty, the coefficient of variation of the nucleic acid present on the base material may be used. The coefficient of variation means a relative value of the scattering of the numbers (the total copy number of nucleic acids present on the base material) of the cells A supported on the base material, where the scattering occurs, for example, in the case where the cells A containing the nucleic acids are supported on the base material. That is, the coefficient of variation means the supporting accuracy of the number of cells A supported on the base material (the total copy number of nucleic acids present on the base material). The coefficient of variation is a value obtained by dividing the standard deviation a by the average value x. Here, in the case of assuming that a value obtained by dividing the standard deviation a by the average copy number x of nucleic acids present on the base material (hereinafter, may be simply referred to as the "average copy number"; and may be also referred to as the average cell number of the supported cells A or the average copy number of supported nucleic acids) is the coefficient of variation CV, a relational Expression 1 shown below is obtained.

$$CV=\sigma/x \qquad \text{Expression 1}$$

In general, the cells A containing nucleic acids are in a randomly distributed state in the Poisson distribution state in a dispersion solution. Therefore, in the serial dilution method, that is, in the random distribution state in the Poisson distribution, the standard deviation a and the average copy number x can be regarded to satisfy a relational Expression 2 shown below. From these, in the case where the cells A containing nucleic acid are diluted by the serial dilution method and in the case where the coefficient of variation CV (the CV value) of the average copy number x is determined from the standard deviation a and the average copy number x by using Expression 3 shown below, which is derived from Expression 1 and Expression 2 shown above, the results are as shown in Table 1 and FIG. 2. The CV value of the coefficient of variation of the number of molecules having the scattering based on the Poisson distribution can be determined from FIG. 2.

$$\sigma = \sqrt{x} \quad \text{Expression 2}$$

$$CV = \frac{1}{\sqrt{x}} \quad \text{Expression 3}$$

TABLE 1

| Average copy number x | Coefficient of variation CV |
|---|---|
| 1.00E+00 | 100.00% |
| 1.00E+01 | 31.62% |
| 1.00E+02 | 10.00% |
| 1.00E+03 | 3.16% |
| 1.00E+04 | 1.00% |
| 1.00E+05 | 0.32% |
| 1.00E+06 | 0.10% |
| 1.00E+07 | 0.03% |
| 1.00E+08 | 0.01% |

Figure 2:
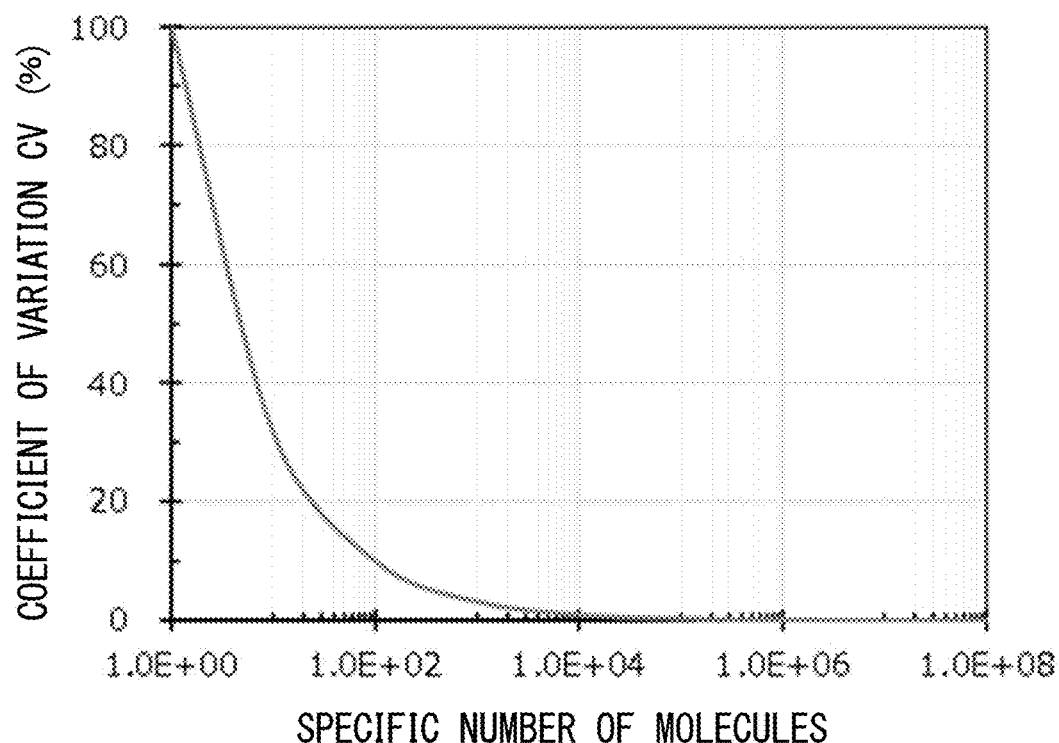
FIG. 2 is a graph showing the relationship between the number of molecules scattered based on the Poisson distribution and the coefficient of variation CV.

From the results of Table 1 and FIG. 2, for example, in the case where the cell A containing one copy of a nucleic acid per cell is used and in the case where 100 cells of the cell A (that is, 100 copies of the nucleic acid) are supported on the base material by a serial dilution method, it can be found that the number (the total copy number of nucleic acids present on the base material) of the cells A finally supported on the carrier has a coefficient of variation (a CV value) of at least 10% even in the case where the accuracy of other factors is ignored.

Regarding the number of cells A, the CV value of the coefficient of variation and the average cell number x of the cells A supported on the base material preferably satisfy the following expression, $CV < 1/\sqrt{x}$, and more preferably $CV < \frac{1}{2}\sqrt{x}$.

Regarding the total copy number of nucleic acids present on the base material, the CV value of the coefficient of variation and the average copy number x of nucleic acids present on the base material preferably satisfy the following expression, $CV < 1/\sqrt{x}$, and more preferably $CV < \frac{1}{2}\sqrt{x}$.

As the information on uncertainty, in the case where there are a plurality of carriers on which the cell A containing a nucleic acid is supported, it is preferable to use the information on uncertainty of the carrier as a whole, based on the specific number of cells supported on the carrier (the specific number of copies of the nucleic acid present on the base material).

There are several possible factors that cause uncertainty, and examples thereof include, in the case where the cells A into which a nucleic acid has been introduced are counted and supported on a base material, the number of nucleic acids in a cell (for example, the change in the number of nucleic acids due to the cell cycle), means (including the result of the operation of each portion of the inkjet device, the device that controls the operation timing of the inkjet device, and the like, such as the number of cells contained in the liquid droplets in the case where the cell suspension is made into liquid droplets) for arranging cells on the base material, the frequency of cells being arranged in the appropriate position on the carrier (for example, the number of cells arranged on the base material), and the contamination due to mixing of the nucleic acid (contamination by a contaminant, may be referred to as "contamination" hereinafter) in a cell suspension caused by cell destruction in the cell suspension.

Examples of the information on a nucleic acid include the information on the species from which the nucleic acid is derived, the information on the composition and the sequence of the nucleic acid, and the information regarding the copy number of the nucleic acid. Examples of the information regarding the copy number of the nucleic acid include the information regarding the copy number of the nucleic acid contained in the cell A, and the information on uncertainty of the copy number of the nucleic acid present on the base material.

[Cell A]

The cell A is a structural and functional unit that forms an organism. The cell A is not particularly limited, and can be appropriately selected depending on the intended purpose. Examples thereof include a eukaryotic cell, a prokaryotic cell, a cell of a multicellular organism, and a cell of a unicellular organism. One kind of cell may be used alone, or two or more thereof may be used in combination.

The eukaryotic cell is not particularly limited, and can be appropriately selected depending on the intended purpose. Examples thereof include an animal cell, an insect cell, a plant cell, a fungal cell, algae, and protozoa. One kind thereof may be used singly, or two or more kinds thereof may be used in combination. Among them, an animal cell or a fungal cell is preferable.

Examples of the animals from which animal cells are derived include fish, amphibians, reptiles, birds, and mammals, but mammals are preferable. Examples of mammals include humans, monkeys, marmosets, dogs, cows, horses, sheep, pigs, rabbits, mice, rats, guinea pigs, and hamsters, but humans are preferable.

The animal cell may be an adhesive cell or a floating cell. The adhesive cell may be a primary cell collected directly from tissues or organs, or may be a passaged cell of the primary cell collected directly from tissues or organs over several generations, may be a differentiated cell, or may be an undifferentiated cell.

The differentiated cell is not particularly limited, and can be appropriately selected depending on the intended purpose. Examples thereof include an endothelial cell such as a hepatocyte, which are the parenchymal cell of the liver, a stellate cell, a Kupffer cell, a vascular endothelial cell, a sinusoidal endothelial cell, or a corneal endothelial cell; an epidermal cell such as a fibroblast, an osteoblast, an osteoclast, a periodontal ligament-derived cell, or an epidermal keratinocyte; an epithelial cell such as a tracheal epithelial cell, a gastrointestinal epithelial cell, a cervical epithelial cell, or a corneal epithelial cell; a breast cell, a pericyte; a muscle cell such as a smooth muscle cell or a myocardial cell; a renal cell, a pancreatic islet of Langerhans cell; a nerve cell such as a peripheral nerve cell or an optic nerve cell; and a cartilage cell and a bone cell.

The undifferentiated cell is not particularly limited, and can be appropriately selected depending on the intended purpose. Examples thereof include a totipotent stem cell such as an embryonic stem cell (an ES cell) or an induced pluripotent stem cell (an iPS cell); a pluripotent stem cell such as a mesenchymal stem cell; and a unipotent stem cell such as a vascular endothelial precursor cell.

The fungal cell is not particularly limited, and can be appropriately selected depending on the intended purpose. Examples thereof include molds and yeasts. One kind thereof may be used singly, or two or more kinds thereof may be used in combination. Among them, yeast is preferable since the cell cycle can be regulated and a haploid can be used. The cell cycle means the period in which cell division occurs when cells proliferate, and cells (daughter cells) generated by cell division become cells (mother cells) that undergo cell division again to produce new daughter cells.

The yeast is not particularly limited, and can be appropriately selected depending on the intended purpose. For example, the yeast is preferably one that has been synchronously cultured in the G0/G1 phase and arrested in the G1 phase. Further, the yeast is, for example, preferably a Bar1 gene-deficient yeast having increased sensitivity to a pheromone (a sex hormone) that controls the cell cycle in the G1 phase. In the case where the yeast is a Bar1 gene-deficient yeast, the abundance ratio of the yeast whose cell cycle cannot be controlled can be reduced, and thus an increase in the copy number of the nucleic acid in the cell or the like can be prevented.

The prokaryotic cell is not particularly limited, and can be appropriately selected depending on the intended purpose. Examples thereof include Eubacteria such as *Eubacteria coli* and archaea. One kind thereof may be used singly, or two or more kinds thereof may be used in combination.

The cell A is preferably a dead cell. In the case of being a dead cell, it is possible to prevent the progression of cell division after preparative isolation and to prevent the change in the amount of intracellular nucleic acid. It is preferable that the cell A emit light when receiving light. In the case where the cells are cells capable of emitting light when receiving light, it is possible to cause the cells to land in the well while the number of cells is controlled with high accuracy.

It is preferable that the cell A emit light when receiving light. Light-receiving means receiving light. Light emission by a cell is detected by an optical sensor. The optical sensor means a passive type sensor that collects, with a lens, any one of visible light that can be seen by the human eye, near infrared light having a longer wavelength than visible light, short wavelength infrared light, and light up to the thermal infrared light region, and then acquires the shape or the like of the cell of interest as image data.

The cell capable of emitting light when receiving light is not particularly limited, and can be appropriately selected depending on the intended purpose. Examples thereof include a cell stained with a fluorescent dye, a cell expressing a fluorescent protein, and a cell labeled with a fluorescently labeled antibody. The portion stained with the fluorescent dye, the portion expressing the fluorescent protein, and the portion labeled with the fluorescently labeled antibody in the cell is not particularly limited, and examples thereof include the entire cell, cell nucleus, and cell membrane.

Examples of the fluorescent dye include fluoresceins, azos, rhodamines, coumarins, pyrenes, and cyanines. The fluorescent dye may be used alone or in a combination of two or more thereof. Among them, fluoresceins, azos, rhodamines, or cyanines are preferable, and eosin, Evans blue, trypan blue, rhodamine 6G, rhodamine B, rhodamine 123, or Cy3 is more preferable.

As the fluorescent dye, a commercially available product can be used. Examples of the commercially available product include product name: Eosin Y (manufactured by FUJIFILM Wako Pure Chemical Corporation), product name: Evans Blue (manufactured by FUJIFILM Wako Pure Chemical Corporation), product Name: Trypan Blue (manufactured by FUJIFILM Wako Pure Chemical Corporation), Product name: Rhodamine 6G (manufactured by FUJIFILM Wako Pure Chemical Corporation), Product name: Rhodamine B (manufactured by FUJIFILM Wako Pure Chemical Corporation), and product name: Rhodamine 123 (manufactured by FUJIFILM Wako Pure Chemical Corporation).

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. The fluorescent protein may be used alone or in a combination of two or more thereof.

The fluorescently labeled antibody is not particularly limited as long as it can bind to the target cell and is fluorescently labeled, and can be appropriately selected depending on the intended purpose. Examples thereof include a FITC-labeled anti-CD4 antibody and a PE-labeled anti-CD8 antibody. The fluorescently labeled antibody may be used alone or in a combination of two or more thereof.

The volume-average cell size of cells is preferably 30 μm or less, more preferably 10 μm or less, and particularly preferably 7 μm or less in the free state. In the case where the volume-average cell size is 30 μm or less, cells can be suitably used for a liquid droplet-ejecting means, such as an inkjet method or a cell sorter.

The volume-average cell size of cells can be measured by, for example, the following measuring method. In the case where yeast is used as cells, 10 μL of the prepared dispersion solution of the stained yeast is taken out, placed on a plastic slide made of PMMA, and the volume-average cell size is measured using an automatic cell counter (trade name: Countess Automated Cell Counter, manufactured by Invitrogen) or the like. The number of cells can also be determined by the same measuring method.

The density of cells in the cell suspension is not particularly limited, and can be appropriately selected depending on the intended purpose, but the density is preferably $5 \times 10^4$ cells/mL or more and $5 \times 10^8$ cells/mL or less and more preferably $5 \times 10^4$ cells/mL or more and $5 \times 10^7$ cells/mL or less. In the case where the cell density is in the above range, the ejected liquid droplets can reliably contain cells. The cell density can be measured using an automatic cell counter (trade name: Countess Automated Cell Counter, manufactured by Invitrogen) or the like in the same manner as the measuring method for the volume-average cell size.

The cell A and the cell containing the detection target gene are preferably derived from the same species or are the same kind of cell, and more preferably derived from the same species and are the same kind of cell. As a result, the nucleic acid can be extracted from the cells A under conditions of the detection target gene, and thus more accurate extraction efficiency can be achieved.

Further, in the carrier of the present embodiment, a form other than the cell can be used as the cell A, instead of the above-described cell, as long as it can reproduce the same conditions as those of the cell. Examples of the form other than the cell include forms such as a liposome, a microcapsule, a virus, a droplet, and an emulsion.

(Liposome)

The liposome is a lipid vesicle formed from a lipid bilayer containing lipid molecules and specifically means a closed lipid-containing vesicle which has a space separated from the outside by a lipid bilayer formed based on the polarities of the hydrophobic group and hydrophilic group of the lipid molecule.

The liposome is a closed vesicle formed by a lipid bilayer using lipids and has an aqueous phase (an inner aqueous phase) in the space of the closed vesicle. The inner aqueous phase contains water and the like. The liposomes may be a single lamella (a single-layer lamella, a uni-lamella, a single-layered bilayer membrane) or a multi-layered lamella (a multi-lamella, multiple bilayer membranes having an onion-like structure, where each layer is partitioned by a watery layer).

The liposome is not limited as long as it can encapsulate nucleic acid, and the form thereof is not particularly limited. "Encapsulation" means that the nucleic acid is contained in the inner aqueous phase or the membrane itself with respect to the liposome. Examples of the form thereof include a form in which a nucleic acid is encapsulated in a closed space formed by the membrane and a form in which a nucleic acid is encapsulated in the membrane itself, and a combination thereof may be used.

The size of the liposome (the average size) is not particularly limited as long as a nucleic acid can be encapsulated and is the same as the size of the cell containing the detection target gene. In addition, the shape thereof is preferably a spherical shape or a shape similar thereto.

The component (the membrane component) constituting the lipid bilayer of the liposome is selected from lipids. As the lipid, any lipid can be used as long as it is soluble in a mixed solvent of a water-soluble organic solvent and an ester-based organic solvent. Specific examples of the lipid include a phospholipid, a lipid other than the phospholipid, cholesterols, and derivatives thereof. These components may be used alone or in a combination of two or more kinds thereof.

(Microcapsule)

The microcapsule means a fine particle having a wall material and a hollow structure, and a nucleic acid can be encapsulated in the hollow structure. The microcapsule is not particularly limited, and the wall material, the size, and the like can be appropriately selected according to the intended purpose.

Examples of the wall material of the microcapsule include a polyurethane resin, polyurea, a polyurea-polyurethane resin, a urea-formaldehyde resin, a melamine-formaldehyde resin, polyimide, polyester, polysulfone amide, polycarbonate, polysulfinate, epoxyri, acrylic acid ester, methacrylic acid ester, vinyl acetate, and gelatin. One kind thereof may be used singly, or two or more kinds thereof may be used in combination.

The size of the microcapsule is not particularly limited as long as a nucleic acid can be encapsulated and is the same as the size of the cell containing the detection target gene, and can be appropriately selected depending on the intended purpose. The method for producing a microcapsule is not particularly limited, and can be appropriately selected depending on the intended purpose. Examples thereof include an in-situ method, an interfacial polymerization method, and a coacervation method.

[Nucleic Acid]

In general, the nucleic acid means a high-molecular-weight organic compound in which nitrogen-containing bases derived from purine or pyrimidine, sugar, and phosphoric acid are regularly bonded, and includes a nucleic acid analog and the like. The nucleic acid is not particularly limited, and can be appropriately selected depending on the intended purpose. Examples thereof include DNA, RNA, and cDNA. The nucleic acid may be a fragment of a nucleic acid or may be incorporated into a nucleic acid a in the nucleus of the cell A but is preferably incorporated into a nucleic acid a in the nucleus of the cell A.

The sequence of the nucleic acid may be a sequence derived from any organism of a eukaryote, a prokaryote, a multicellular organism, and a unicellular organism. Examples of the eukaryotes include animals, insects, plants, fungi, algae, and protozoa. Examples of the animals include the same animals as those exemplified in the "cell A" described above. Among them, a mammal is preferable, and a human is more preferable.

The artificially synthesized nucleic acid means a nucleic acid obtained by artificial synthesis, which is composed of the same constitutional components (base, deoxyribose, phosphoric acid) as those of the naturally occurring DNA or RNA. The artificially synthesized nucleic acid may be, for example, a nucleic acid having a base sequence encoding a protein or may be a nucleic acid having any base sequence.

Examples of the nucleic acid analog or nucleic acid fragment analog include a nucleic acid or nucleic acid fragment to which a non-nucleic acid component is bound, or a nucleic acid or nucleic acid fragment (for example, a primer or a probe labeled with a fluorescent dye or a radioisotope) which is labeled with a labeling agent such as a fluorescent dye or an isotope, and an artificial nucleic acid (for example, PNA, BNA, or LNA) in which the chemical structure of a part of the nucleotides constituting the nucleic acid or nucleic acid fragment is changed.

The form of the nucleic acid is not particularly limited, and can be appropriately selected depending on the intended purpose. Examples thereof include a double-stranded nucleic acid, a single-stranded nucleic acid, and a partially double-stranded or single-stranded nucleic acid, and may be a circular or linear plasmid. In addition, the nucleic acid may have a modification or a mutation.

The nucleic acid preferably has a specific base sequence which is clearly revealed. The specific base sequence is not particularly limited, and can be appropriately selected depending on the intended purpose. Examples thereof include a base sequence used for genetic disease testing, a non-natural base sequence that does not exist in nature, a base sequence derived from an animal cell, a base sequence derived from a plant cell, a base sequence derived from a fungal cell, a base sequence derived from a bacterium, and a base sequence derived from a virus. One kind thereof may be used singly, or two or more kinds thereof may be used in combination.

The nucleic acid may be a nucleic acid derived from the cell to be used or may be a nucleic acid introduced by gene transfer. The kind of nucleic acid contained in the cell A may be one or more kinds, but one kind is preferable.

The copy number of the nucleic acid contained in the cell A can be, for example, 1, 2, 3, 4, 5, 6, 7, 8, 9, 10, 15, 20, 30, 50, or 100 copies. Further, in the case where two or more cells A are supported on the base material, the copy numbers of nucleic acids contained in the cells A may be the same or different from each other but are preferably the same since the carrier can be efficiently manufactured.

Among the above, it is preferable that one cell A contain one copy of nucleic acid. In this case, "the number of cells A" can be regarded as "the total copy number of nucleic acids present on the base material", and thus the total copy number of nucleic acids present on the base material can be more easily counted.

In the case where a nucleic acid incorporated into the nucleus of a cell by gene transfer is used as the nucleic acid, it is preferable to confirm that a specific number of copies (for example, 1 copy) of a nucleic acid be introduced into one cell. The method for confirming that a specific number of copies of a nucleic acid have been introduced is not particularly limited, and can be appropriately selected depending on the intended purpose. Examples thereof include sequencing, a PCR method, and Southern blotting.

In the case of introducing a nucleic acid into the nucleus of a cell, the method for gene transfer is not particularly limited as long as the desired number of copies of a specific nucleic acid sequence can be introduced into the target location. Examples thereof include homologous recombination, CRISPR/Cas9, CRISPR/Cpf1, TALEN, Zinc finger nuclease, Flip-in, and Jump-in. Alternatively, the nucleic acid may be introduced into the nucleus of the cell in the form of a plasmid, artificial chromosome, or the like. For example, in the case where yeast (a yeast cell) is used as the cell, homologous recombination is preferable among them from the viewpoint of high efficiency and ease of control.

The nucleic acid may be composed of the same sequence as that of the detection target gene or may be composed of a different sequence. In the case where the carrier of the present embodiment is used to extract a nucleic acid from the cell A and detect the nucleic acid in a reaction space different from that of the cell sample containing the detection target gene, the nucleic acid preferably has the same sequence as the detection target gene since the nucleic acid can be extracted and detected under conditions closer to the detection target gene. On the other hand, in the case where the carrier of the present embodiment is used to extract a nucleic acid from the cell A and detect the nucleic acid in the same reaction space as the cell sample containing the detection target gene, the nucleic acid preferably has a sequence different from that of the detection target gene. In the case where the nucleic acid is composed of a sequence different from that of the detection target gene, the length of the nucleic acid is preferably the same as the length of the detection target gene, or the nucleic acid is preferably longer or shorter than the detection target gene by about 1 base to 10 bases, and preferably by about 1 base to 5 bases, for extracting and detecting the nucleic acid under conditions closer to the detection target gene. Further, for the same reason as for the base length, the GC content of the nucleic acid is preferably the same as that of the detection target gene, or the GC content of the nucleic acid is preferably higher or lower than the GC content of the detection target gene by 1% to 5%, and preferably by 1% to 3%.

[Base Material]

The base material 5 has the supporting part 2. The entire base material 5 including the supporting part 2 may be made of a water-decomposable material, or only the supporting part 2 may be made of a water-decomposable material and the other part thereof may be made of a material having no water-decomposability (a non-water-decomposable material). The non-water-decomposable material that can be used as the base material is preferably a material that does not have cytotoxicity or has relatively low cytotoxicity. Specific examples thereof include polyphosphazene, poly(vinyl alcohol), polyamide (for example, nylon), polyesteramide, poly (amino acid), polyanhydride, polysulfone, polycarbonate, polyacrylate (an acrylic resin), polyalkylene (for example, polyethylene), polyacrylamide, polyalkylene glycol (for example, polyethylene glycol), polyalkylene oxide (for example, polyethylene oxide), polyalkylene terephthalate (for example, polyethylene terephthalate), polyorthoester, polyvinyl ether, polyvinyl ester, polyvinyl halide, polyvinyl pyrrolidone, polyester, polysiloxane, polyurethane, polyhydroxy acid (for example, polylactide and polyglycolide), poly(hydroxybutyrate), poly(hydroxyvaleric acid), poly[lactide-co-(ε-caprolactone)], poly[glycolide-co-(ε-caprolactone)], poly(hydroxyalkanoate), and copolymers thereof, but are not limited thereto.

The shape of the base material is not particularly limited, and may be sheet-shaped or spherical. The size thereof is also not particularly limited, and can be appropriately set depending on the size of the reaction space in which a nucleic acid is extracted and tested.

<Manufacturing Method for Carrier>

The manufacturing method for the carrier of the present embodiment (hereinafter, may be simply referred to as "the manufacturing method of the present embodiment") will be described below.

The manufacturing method of the present embodiment includes an incorporation process of incorporating a specific number of copies of a nucleic acid into the nucleic acid a in the nucleus of the cell A, and a nucleic acid-supporting process of preparing liquid droplets containing one cell in which a specific number of copies of a nucleic acid are incorporated into the nucleic acid a in the nucleus and supporting a specific number of cells on the base material by controlling the number of the liquid droplets. The manufacturing method of the present embodiment preferably further includes a cell suspension purification process and a cell number-measuring process, and more preferably further include a process of calculating the certainty of the copy number of the nucleic acid present on the base material, an output process, and a recording process, where the uncertainty is estimated in the cell suspension generation process, the nucleic acid-supporting process, and the cell number-measuring process, and further includes another process as necessary.

[Incorporation Process]

In the incorporation process, a specific number of copies of a nucleic acid are incorporated into the nucleic acid a in the nucleus of the cell A.

The copy number of the nucleic acid incorporated into the nucleic acid a in the nucleus of the cell A is not particularly limited as long as it is the specific copy number, but it is preferably one copy from the viewpoint of introduction efficiency.

Examples of the method for incorporating a nucleic acid into the nucleic acid a in the nucleus of the cell A include the same methods as those exemplified as the "method for gene transfer" in the above-described "nucleic acid".

[Nucleic Acid-Supporting Process]

In the nucleic acid-supporting process, liquid droplets containing one cell A in which a nucleic acid is incorporated into the nucleic acid a in the nucleus are prepared, and a specific number of cells A are supported on the base material by controlling the number of the liquid droplets. Liquid droplets means a single mass of liquid that is formed by surface tension.

Preparation of and filling with liquid droplets are achieved, for example, by ejecting, as liquid droplets, a cell suspension containing the cells A in which a nucleic acid is incorporated into the nucleic acid a in the nucleus and by sequentially landing the liquid droplets on the base material. "Ejecting" means causing a cell suspension to fly as liquid droplets. "Sequentially" means one after another in order. "Landing" means causing liquid droplets to reach the base material.

The base material may be any one as long as it has a supporting part made of a water-decomposable material, and specific examples thereof include the same base materials as those described in the above-described "base material".

As the ejecting means, means for ejecting a cell suspension as liquid droplets (hereinafter, may also be referred to as an "ejection head") can be suitably used.

Examples of the method for ejecting a cell suspension as liquid droplets include an on-demand type method and a continuous type method in the inkjet method. Among these, in the case of the continuous type method, the dead volume of the cell suspension used tends to increase since empty ejection is continued until a stable ejection state is reached, the amount of liquid droplets is adjusted, and liquid droplets are continuously formed even in the case of moving between wells. In the present embodiment, it is preferable to reduce the influence of the dead volume from the viewpoint of adjusting the number of cells. For this reason, in the above two types of methods, the on-demand type method is more preferable.

Examples of the on-demand type method include a plurality of known methods such as a pressure application type method in which a liquid is ejected by applying pressure to the liquid, a thermal type method in which a liquid is ejected by film boiling due to heating, and an electrostatic type method in which liquid droplets are formed by drawing in the liquid droplets by electrostatic attraction. Among these, a pressure application type method type is preferable for the following reasons.

In the electrostatic type method, it is necessary to install an electrode to face an ejection part that retains a cell suspension and forms liquid droplets. In the manufacturing method of the present embodiment, plates for receiving liquid droplets are disposed to face each other, and thus it is preferable that electrodes not be arranged in order to increase the degree of freedom in the plate configuration. In the thermal type method, local heating occurs, and thus there is a concern about the influence on cells, which are biological material, and scorching (cogation) on the heater part. Since the influence of heat depends on the content and the use of the plate, it is not necessary to exclude the influence of heat sweepingly, but the pressure application type method is preferable in the thermal type method since there is no concern about scorching on the heater part.

Examples of the pressure application type method include a method for applying pressure to a liquid using a piezo element and a method for applying pressure by a valve such as a solenoid valve. Examples of the configuration of the liquid droplet generation device that can be used for the liquid droplet ejection of a cell suspension are shown in FIGS. 3 to 5.

Figure 3:
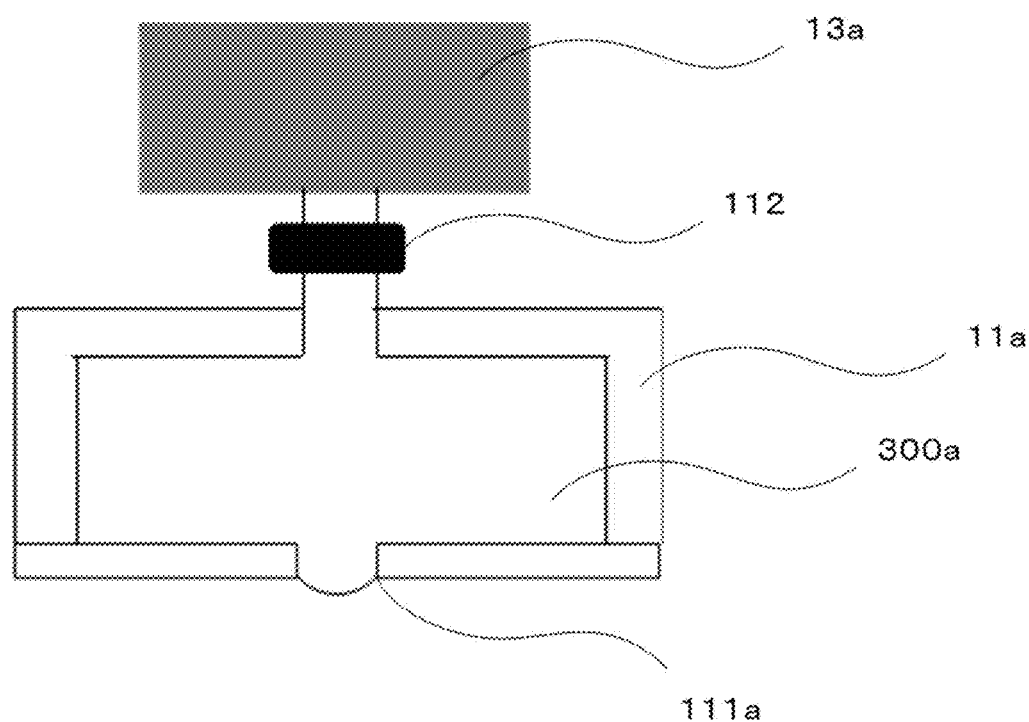
FIG. 3 is a schematic view showing one example of a solenoid valve type ejection head.

FIG. 3 is a schematic view showing one example of a solenoid valve type ejection head. The solenoid valve type ejection head includes an electric motor 13a, a solenoid valve 112, a liquid chamber 11a, a cell suspension 300a, and a nozzle 111a. As the solenoid valve type ejection head, for example, a dispenser manufactured by Techelan LLC or the like can be preferably used.

Figure 4:
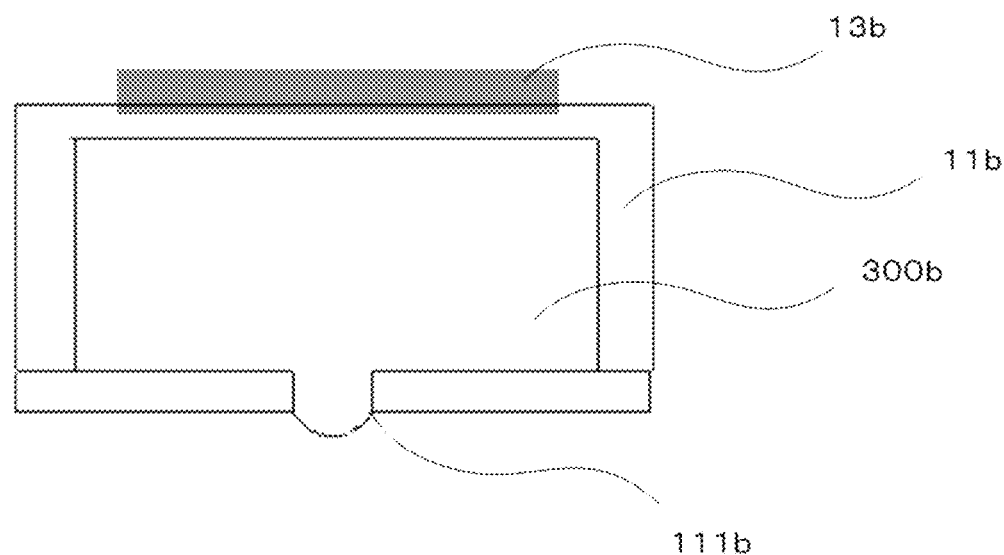
FIG. 4 is a schematic view showing one example of a piezo type ejection head.
Figure 5:
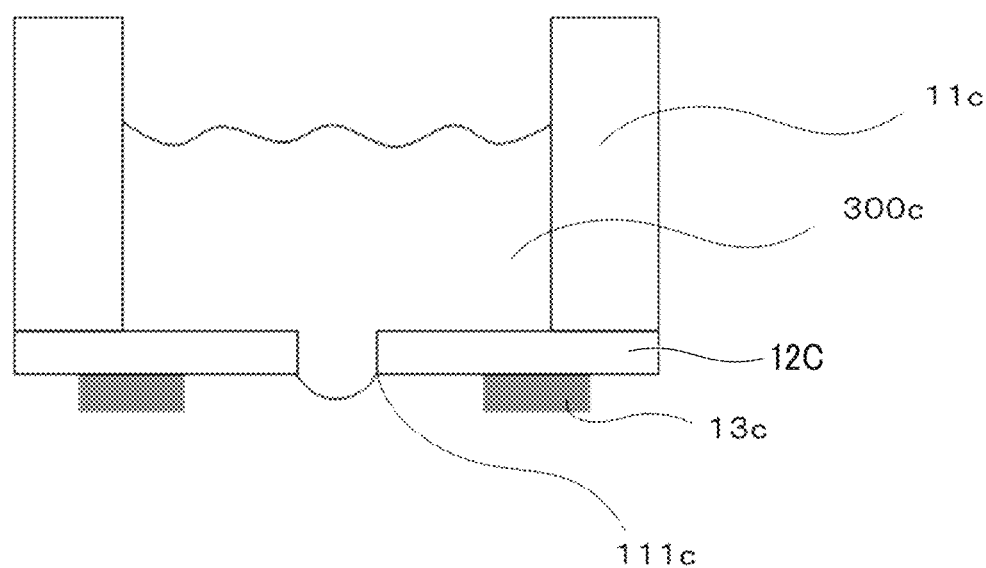
FIG. 5 is a schematic view showing a modified example of the piezo type ejection head in FIG. 4.

FIG. 4 is a schematic view showing one example of a piezo type ejection head. The piezo type ejection head has a piezoelectric element 13b, a liquid chamber 11 b, a cell suspension 300b, and a nozzle 111b. As the piezo type ejection head, a single cell printer manufactured by Cytena Gmbh or the like can be preferably used.

Although any one of these ejection heads can be used, the piezo type method is preferably used to increase the throughput of plate formation since it is not possible to repeatedly form liquid droplets at high speed with the pressure application type method using a solenoid valve.

Further, in the piezo type ejection head in which the general piezoelectric element 13b is used, non-uniformity of cell concentration due to sedimentation and nozzle clogging may occur.

For this reason, as a more preferable configuration, configurations shown in FIG. 5 or the like can be mentioned. FIG. 5 is a schematic view showing a modified example of the piezo type ejection head in FIG. 4 in which a piezoelectric element is used. The ejection head of FIG. 5 has a piezoelectric element 13c, a liquid chamber 11c, a cell suspension 300c, and a nozzle 111c.

In the ejection head of FIG. 5, in the case where a voltage is applied to the piezoelectric element 13c from a control device which is not shown in the figure, compressive stress is applied in the lateral direction of the paper surface, and thus a membrane 12c can be deformed in the vertical direction of the paper surface.

Examples of the method other than the on-demand type method include a continuous type method in which liquid droplets are continuously formed. In the continuous type method, in the case where liquid droplets are pressurized and ejected from the nozzle, a piezoelectric element or a heater provides regular fluctuation, whereby fine liquid droplets can be continuously produced. Further, in the case where the ejection direction of the flying liquid droplets is controlled by applying a voltage, it is possible to select whether to land the liquid droplets on the well or collect the liquid droplets on the collecting part. Such a method is used in a cell sorter or a flow cytometer, and for example, Cell Sorter SH800Z (apparatus name, manufactured by Sony Corporation) can be used.

Figure 6A:
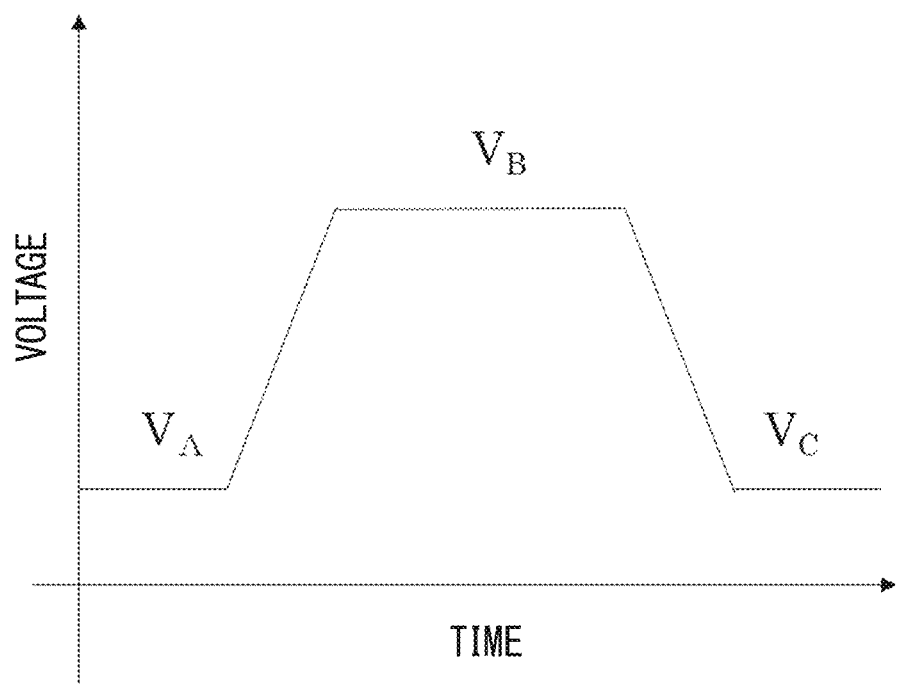
FIG. 6 (a) is a schematic view showing one example of a voltage applied to a piezoelectric element.
Figure 6B:
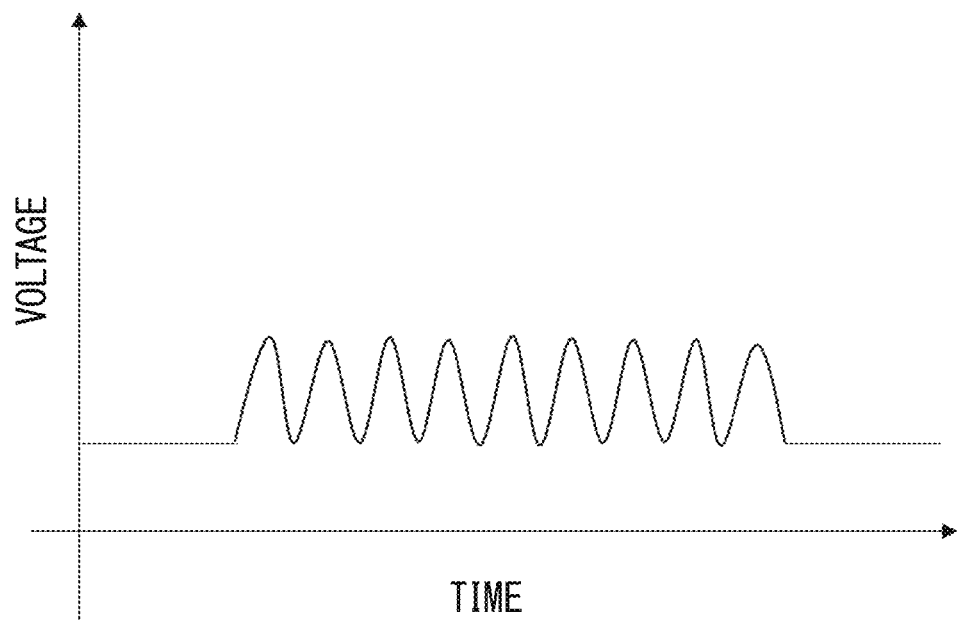

FIG. 6 (a) is a schematic view showing one example of a voltage applied to a piezoelectric element. In addition, FIG. 6 (b) is a schematic view showing another example of a voltage applied to a piezoelectric element. FIG. 6 (a) shows a driving voltage for forming a liquid droplet. It is possible to form liquid droplets by controlling the value of the voltage ($V_A$, $V_B$, $V_C$). FIG. 6 (B) shows the voltage for stirring a cell suspension without ejecting a liquid droplet.

In the case of inputting a plurality of pulses that are not sufficient enough to eject liquid droplets during the period in which liquid droplets are not ejected, it is possible to stir a cell suspension in the liquid chamber, and thus the concentration distribution due to cell sedimentation can be suppressed.

Figure 7A:
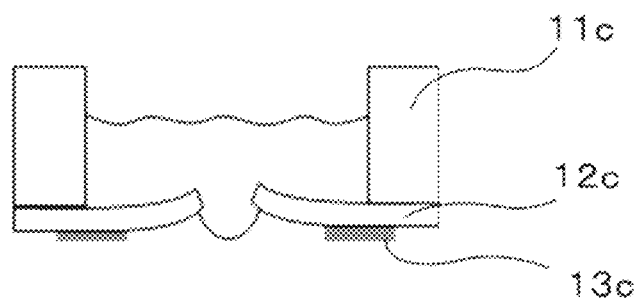
FIGS. 7 (a) to (c) are schematic views showing one example of a state of a liquid droplet.
Figure 7B:
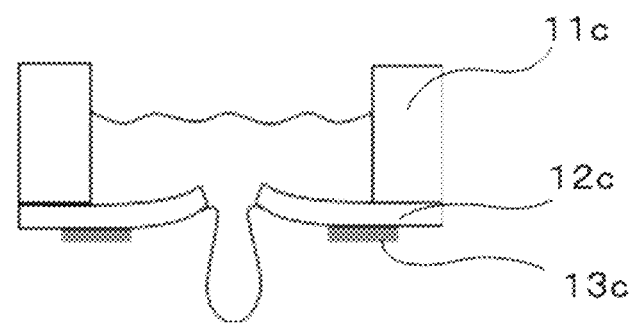
Figure 7C:
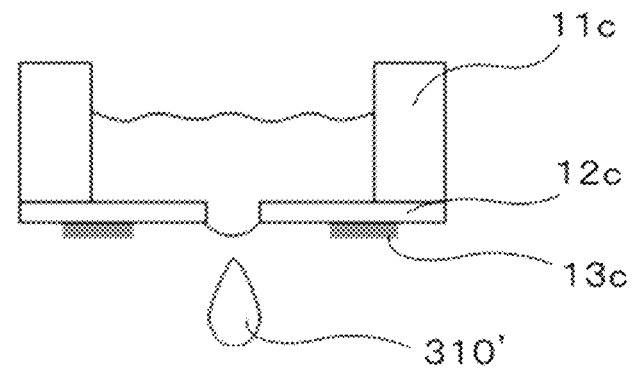

The liquid droplet-forming operation of the ejection head that can be used in the present embodiment will be described below. In the case where a voltage having a pulse form is applied to the upper and lower electrodes formed on the piezoelectric element, the ejection head can eject a liquid droplet. FIGS. 7 (a) to (c) are schematic views showing a state of liquid droplets at each timing.

First, as shown in FIG. 7 (a), in the case of applying a voltage to the piezoelectric element 13c, the membrane 12c is rapidly deformed, whereby a high pressure is generated between the cell suspension retained in the liquid chamber 11c and the membrane 12c, and liquid droplets are forced out of the nozzle part by this pressure.

Next, as shown in FIG. 7 (b), the liquid is continuously ejected from the nozzle part until the pressure is reduced in the upper direction, and the liquid droplets grow. Finally, as shown in FIG. 7 (c), in the case where the membrane 12c returns to its original state, the liquid pressure in the vicinity of the interface between the cell suspension and the membrane 12c decreases, and liquid droplets 310' are formed.

In the manufacturing method of the present embodiment, the liquid droplets may be made to sequentially land on a supporting part made of a water-decomposable material, where the supporting part is provided on the base material, by fixing the base material on a movable stage and combining the driving of the stage and the liquid droplets formation from the ejection head. Here, regarding the movement of the stage, the method for moving the base material has been described, but of course, the ejection head may be moved.

Figure 8:
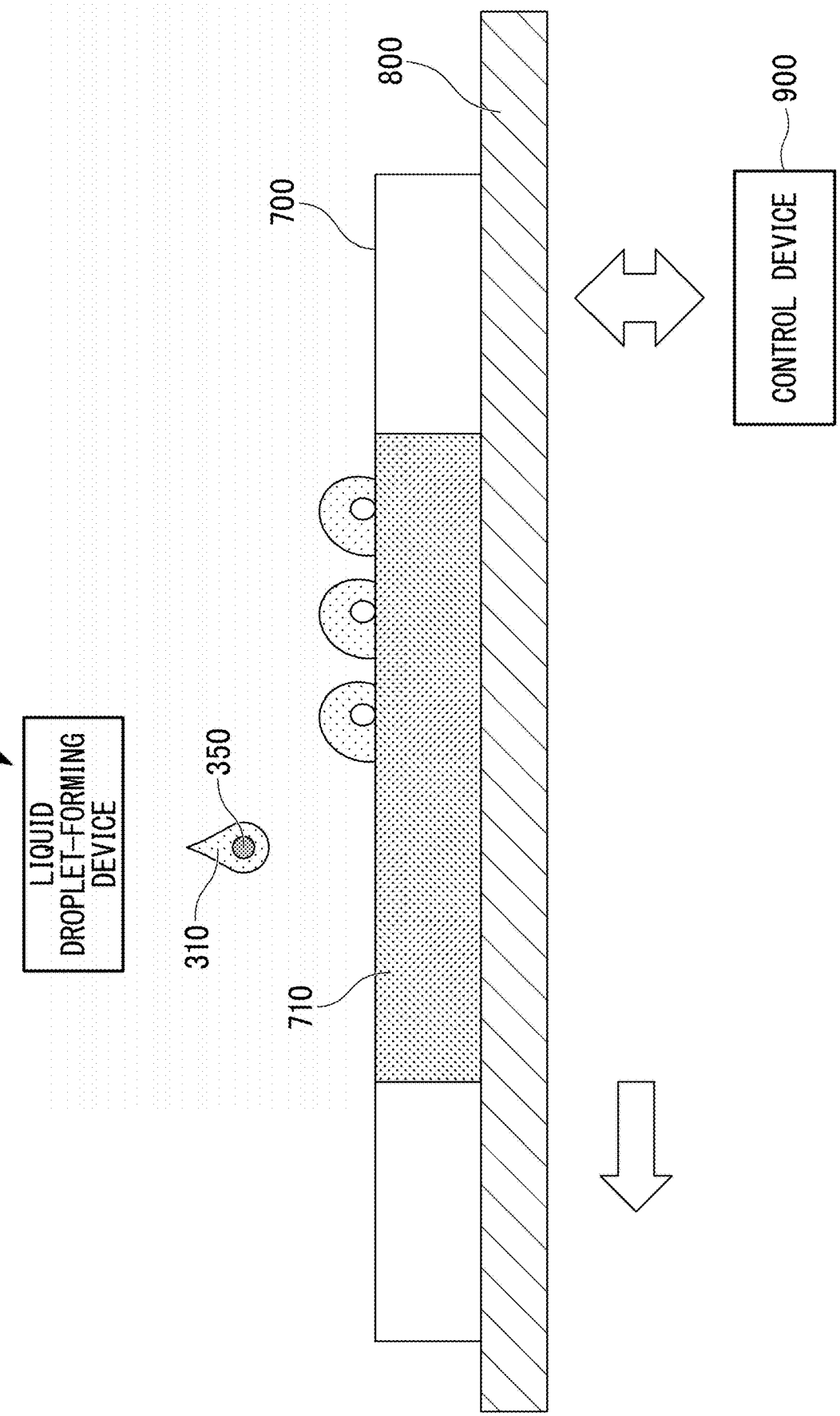
FIG. 8 is a schematic view showing one example of a dispensing device for sequentially applying liquid droplets in a well.

FIG. 8 is a schematic view showing one example of a dispensing device 400 for sequentially landing liquid droplets on a supporting part made of a water-decomposable material, where the supporting part is provided on the base material. As shown in FIG. 8, the dispensing device 400 for landing liquid droplets includes a liquid droplet-forming device 401, a base material 700, a stage 800, and a control device 900.

In the dispensing device 400, the base material 700 is disposed on the stage 800 which is configured to be movable. In the base material 700, a supporting part 710 made of a water-decomposable material, on which the liquid droplets 310 ejected from the ejection head of the liquid droplet-forming device 401 are seated. The control device 900 moves the stage 800 and controls the relative positional relationship between the ejection head of the liquid droplet-forming device 401 and the supporting part 710. As a result, the liquid droplets 310 containing fluorescently stained cells 350 can be sequentially ejected from the ejection head of the liquid droplet-forming device 401 onto the supporting part 710.

The control device 900 can be configured to include, for example, a CPU, a ROM, a RAM, and a main memory. In this case, various functions of the control device 900 can be realized by reading out a program recorded in the ROM or the like into the main memory and executing the program by the CPU. However, a part or all of the control device 900 may be realized only by hardware. Further, the control device 900 may be physically composed of a plurality of devices and the like.

Regarding the liquid droplets to be ejected, it is preferable to cause the liquid droplets to land on the base material so that a plurality of levels are obtained when causing the cell suspension to land on the base material. The plurality of levels means a plurality of standards that serve as standards. Examples of the plurality of levels include, for example, a predetermined concentration gradient of a plurality of cells A, a nucleic acid of which is provided on a base material. The plurality of levels can be controlled using the values measured by the sensor.

[Cell Suspension Generation Process]

The cell suspension generation process is a process of generating a cell suspension which contains a plurality of cells A in which a nucleic acid is introduced into the nucleic acid a in the nucleus, and a solvent. The solvent means a liquid used for dispersing cells. Regarding the cell suspension, the suspension means a solution in which cells are present in the state of being dispersed in a solvent. Generation means creating.

(Cell Suspension)

The cell suspension contains a plurality of cells A in which a nucleic acid is introduced into the nucleic acid a in the nucleus, and a solvent, preferably contains an additive, and further contains other components as necessary. The plurality of cells into which a nucleic acid is introduced into the nucleic acid a in the nucleus are as described in the section of "Cell A".

(Solvent)

The solvent is not particularly limited, and can be appropriately selected depending on the intended purpose. Examples thereof include water, a culture solution, a separation solution, a diluent, a buffer solution, an organic substance solution, an organic solvent, a polymer gel solution, a colloidal dispersion solution, an aqueous electrolyte solution, an aqueous inorganic salt solution, an aqueous metal solution, and a mixed liquid thereof. One kind thereof may be used singly, or two or more kinds thereof may be used in combination. Among them, water or a buffer is preferable, and water, phosphate buffered saline (PBS), or a Tris-EDTA buffer (TE) is preferable.

(Additive)

The additive is not particularly limited, and can be appropriately selected depending on the intended purpose. Examples thereof include a surfactant, a nucleic acid, and a resin. One kind thereof may be used singly, or two or more kinds thereof may be used in combination.

The surfactant can prevent the aggregation between cells and thus improve continuous ejection stability. The surfactant is not particularly limited, and can be appropriately selected depending on the intended purpose. Examples thereof include an ionic surfactant and a nonionic surfactant. One kind thereof may be used singly, or two or more kinds thereof may be used in combination. Among these, a nonionic surfactant is preferable since a protein is not denatured and is deactivated, which depends on the amount added though.

Examples of the ionic surfactant include fatty acid sodium, fatty acid potassium, alpha sulfo fatty acid ester sodium, sodium linear alkylbenzene sulfonate, alkyl sulfate ester sodium, alkyl ether sulfate ester sodium, and sodium alpha olefin sulfonate. One kind thereof may be used singly, or two or more kinds thereof may be used in combination. Of them, sodium fatty acid is preferable, and sodium dodecyl sulfate (SDS) is more preferable.

Examples of the nonionic surfactant include an alkyl glycoside, an alkyl polyoxyethylene ether (Brij series or the like), octylphenol ethoxylate (Triton X series, Igepal CA series, Nonidet P series, Nikkol OP series, or the like), polysorbates (Tween series such as Tween 20), sorbitan fatty acid ester, polyoxyethylene fatty acid ester, an alkyl maltoside, sucrose fatty acid ester, glycoside fatty acid ester, glycerin fatty acid ester, propylene glycol fatty acid ester, and fatty acid monoglyceride. One kind thereof may be used singly, or two or more kinds thereof may be used in combination. Among them, polysorbates are preferable.

The content of the surfactant is not particularly limited, and can be appropriately selected depending on the intended purpose. However, the content of the surfactant is preferably 0.001% by mass or more and 30% by mass or less with respect to the total amount of the cell suspension. In the case where the content is 0.001% by mass or more, the effect of adding the surfactant can be obtained, and in the case where the content is 30% by mass or less, the aggregation of cells A can be suppressed, and thus the copy number of the nucleic acid in the cell suspension can be strictly controlled.

The nucleic acid is not particularly limited as long as it does not affect the detection of the nucleic acid contained in the cell A or the gene to be tested, and can be appropriately selected depending on the intended purpose. Examples thereof include ColE1 DNA. In the case where the nucleic acid is added, it is possible to prevent attachment to the surface of the well or the like, which is used in the case of extracting and detecting the nucleic acid contained in the cell A or the gene to be tested.

The resin is not particularly limited, and can be appropriately selected depending on the intended purpose. Examples thereof include polyethyleneimide.

(Other Components)

Other components are not particularly limited, and can be appropriately selected depending on the intended purpose. Examples thereof include a cross-linking agent, a pH adjusting agent, a preservative, an antioxidant, an osmotic pressure adjusting agent, a wetting agent, and a dispersing agent.

The method for dispersing the cells A is not particularly limited, and can be appropriately selected depending on the intended purpose. Examples thereof include a media type method such as a bead mill, an ultrasonic type method such as an ultrasonic homogenizer, and a method using a pressure difference such as a French press. One kind thereof may be used singly, or two or more kinds thereof may be used in combination. Among these, an ultrasonic type method is preferable since it causes less damage to cells. In the media type method, cell membrane or cell wall may be destroyed, or the media may be mixed as a contaminant since the crushing ability is strong.

The screening method for cell A is not particularly limited, and can be appropriately selected depending on the intended purpose. Examples thereof include screening with wet type classification, a cell sorter, or a filter. One kind thereof may be used singly, or two or more kinds thereof may be used in combination. Among them, screening with a cell sorter or a filter is preferable since the damage to cells is small.

Regarding the cells A, it is preferable to estimate the copy number of the nucleic acid from the number of cells contained in the cell suspension by measuring the cell cycle of the cell. Measuring the cell cycle means quantifying the number of cells affected by cell division. Estimating the copy number of the nucleic acid means obtaining the copy number of the nucleic acid from the number of cells.

The measurement target may not be the number of cells and may be the number of nucleic acids contained. Generally, the number of nucleic acids may be considered to be equal to the number of cells since the cells A into which one copy of the nucleic acid is introduced per one cell A are selected or the nucleic acid is introduced into the cell by genetic recombination. However, since the cell A undergoes cell division at a specific cycle, the replication of the nucleic acid occurs within the cell A. The cell cycle differs depending on the kind of cell A, but in the case of extracting a predetermined amount of solution from the cell suspension and measuring the cycles of a plurality of cells, the expected value for the number of nucleic acids contained in one cell and the certainty of the expected value can be calculated. This can be carried out, for example, by observing the cells A subjected to nuclear staining, with a flow cytometer.

The certainty means a probability of occurrence of a specific event, where the degree of possibility that the specific event will occur is predicted in advance in the case where several events are likely to occur. Calculation means to calculate and obtain a numerical value.

Figure 9:
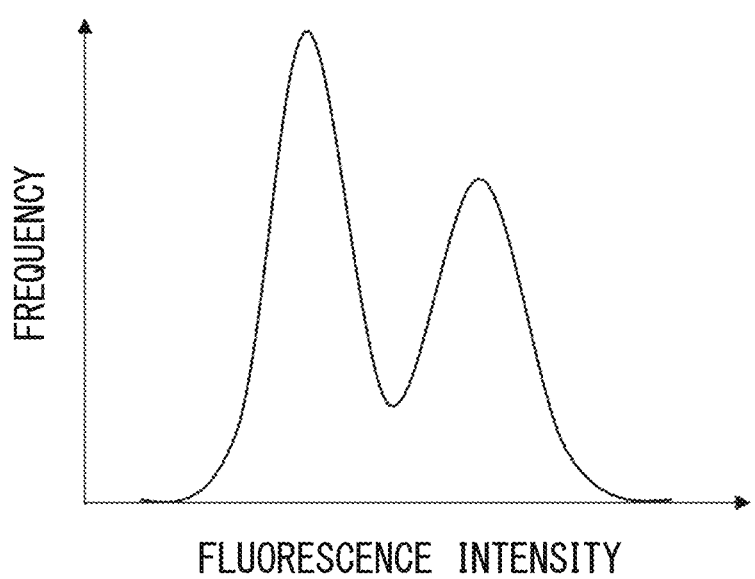
FIG. 9 is a graph showing one example of the relationship between the frequency of DNA-replicated cells and the fluorescence intensity.

FIG. 9 is a graph showing one example of the relationship between the frequency of DNA-replicated cells and the fluorescence intensity. As shown in FIG. 9, since two peaks appear on the histogram depending on the presence or absence of DNA replication, it is possible to calculate the proportion of DNA-replicated cells. From this calculation result, it is possible to calculate the average copy number of the nucleic acid contained in one cell, which is subsequently multiplied by the cell number-measuring result described above, thereby the estimated copy number of the nucleic acid can be calculated.

In addition, it is preferable to perform a treatment for controlling the cell cycle before preparing a cell suspension. In the case where cells are synchronized in the state before or after the occurrence of the above-described replication, it is possible to more accurately calculate the copy number of the nucleic acid from the number of cells.

It is preferable to calculate the certainty (the probability) of the specific copy number to be estimated. In the case where the certainty (probability) is calculated, it is possible to represent and output the certainty as a variance or a standard deviation based on these numerical values. In the case of summing up the effects of a plurality of factors, it is possible to use the square root of sum of squares of the standard deviations, which is commonly used. For example, the correct answer rate of the number of ejected cells, the number of DNA in the cell, the landing rate of the ejected cell that is made to land in the well, and the like can be used as factors. It is also possible to select, among these, an item that has a large influence and to perform a calculation.

[Cell Number-Measuring Process]

The cell number-measuring process is a process of measuring the number of cells contained in the liquid droplets by a sensor after the liquid droplets are prepared and before the liquid droplets are made to land on the base material. The sensor means a device that converts a mechanical, electromagnetic, thermal, acoustic, or chemical property of a natural phenomenon or artificial object, or spatial or temporal information indicated by the above property into a signal of another medium that is easily handled by a human or machine, by applying scientific principles. Measuring the number of cells means counting cells.

The cell number-measuring process is not particularly limited as long as the number of cells contained in the liquid droplet is measured by a sensor after the liquid droplet is ejected and before the liquid droplet is made to land on the supporting part, and can be appropriately selected depending on the intended purpose. The cell number-measuring process may include a treatment for observing cells before ejection and a treatment for counting cells after landing.

For measuring the number of cells contained in the liquid droplet after the liquid droplet is ejected and before the liquid droplet is made to land on the supporting part, it is preferable to observe the cells in the liquid droplet at the timing at which the liquid droplet is present directly above the supporting part where the liquid droplet is predicted to reliably come into contact with the supporting part of the base material.

Examples of the method for observing the cells in the liquid droplet include a method for optically detecting and a method for electrical or magnetic detecting.

(Method for Optically Detecting)

Figure 10:
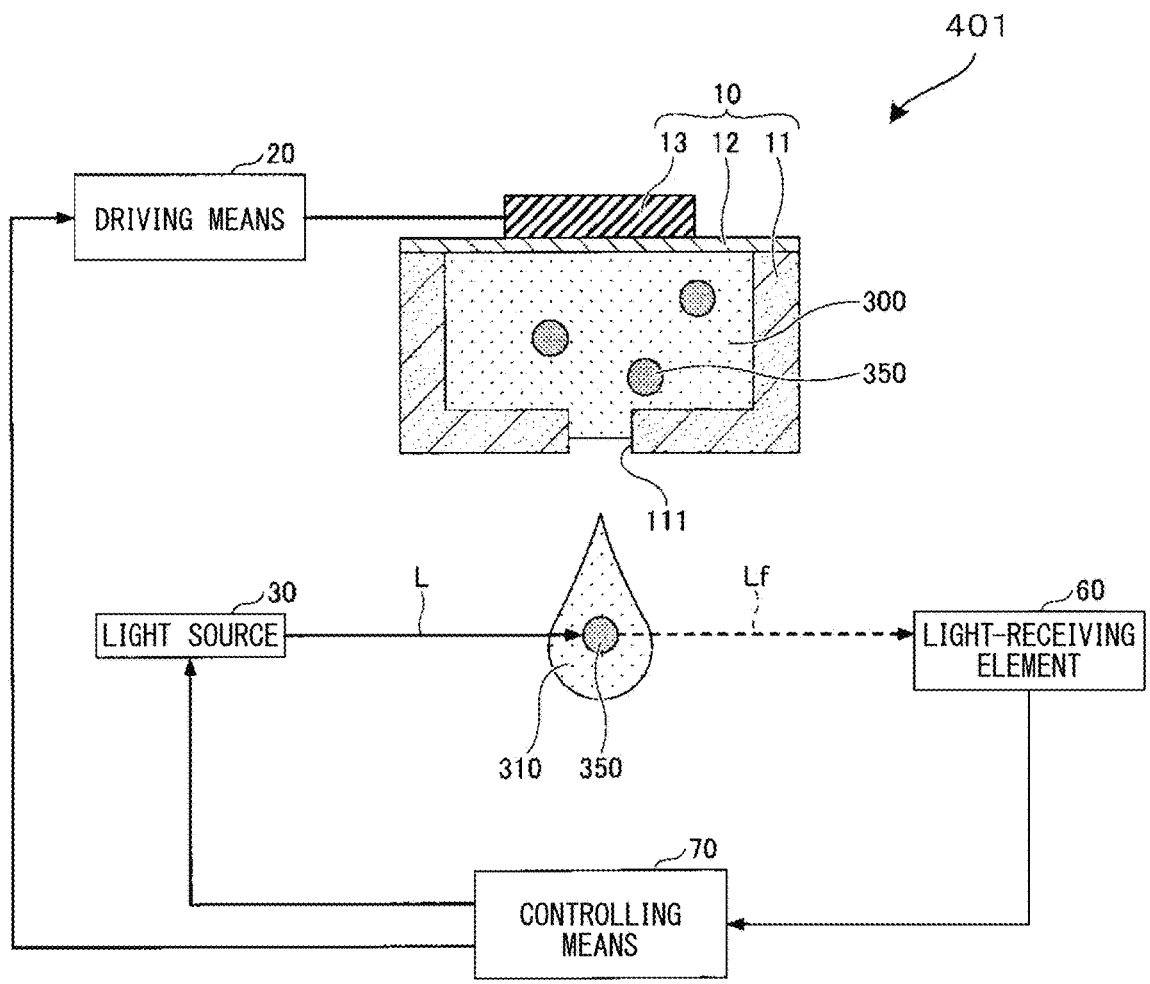
FIG. 10 is a schematic view showing one example of a liquid droplet-forming device.
Figure 14:
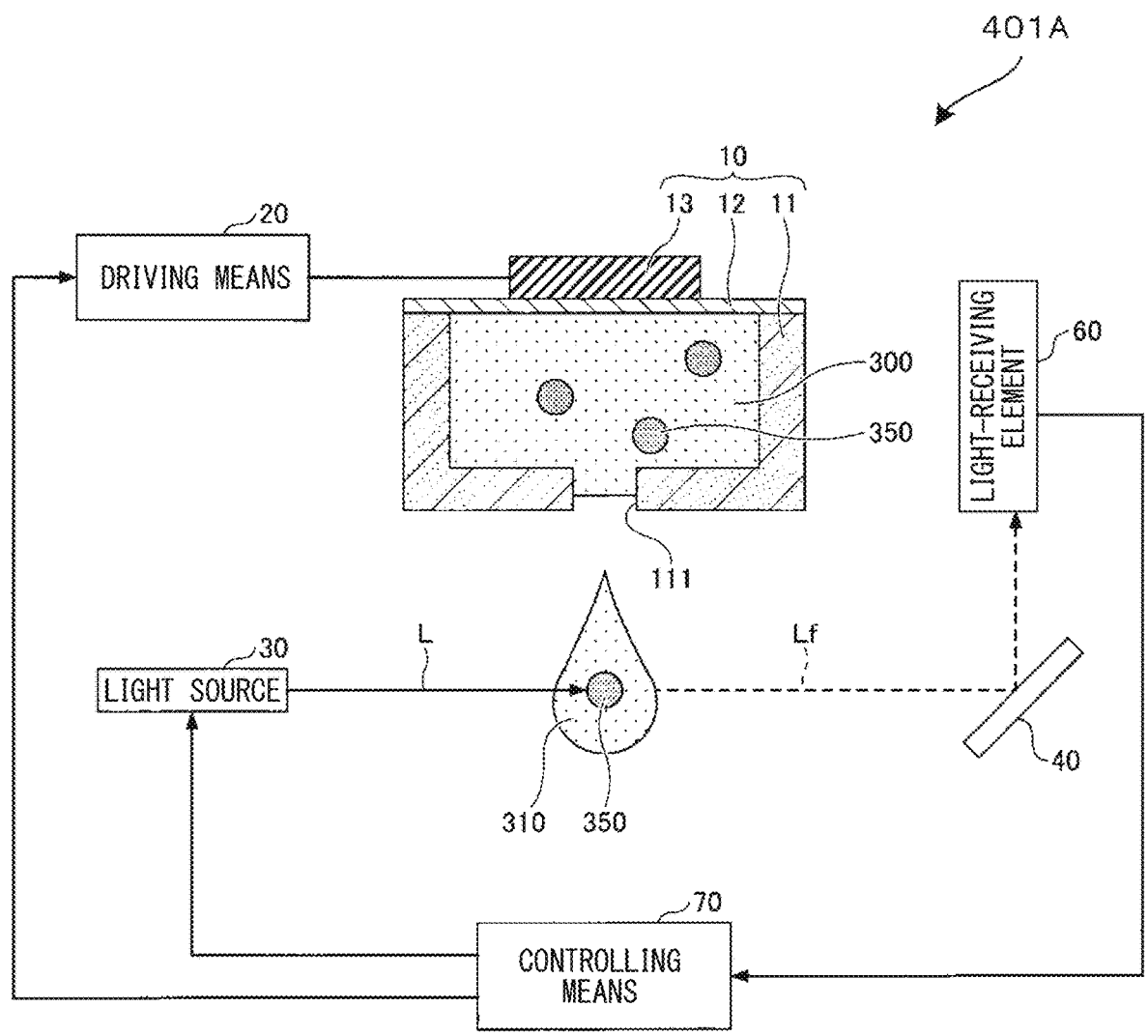
FIG. 14 is a schematic view showing a modified example of the liquid droplet-forming device.
Figure 15:
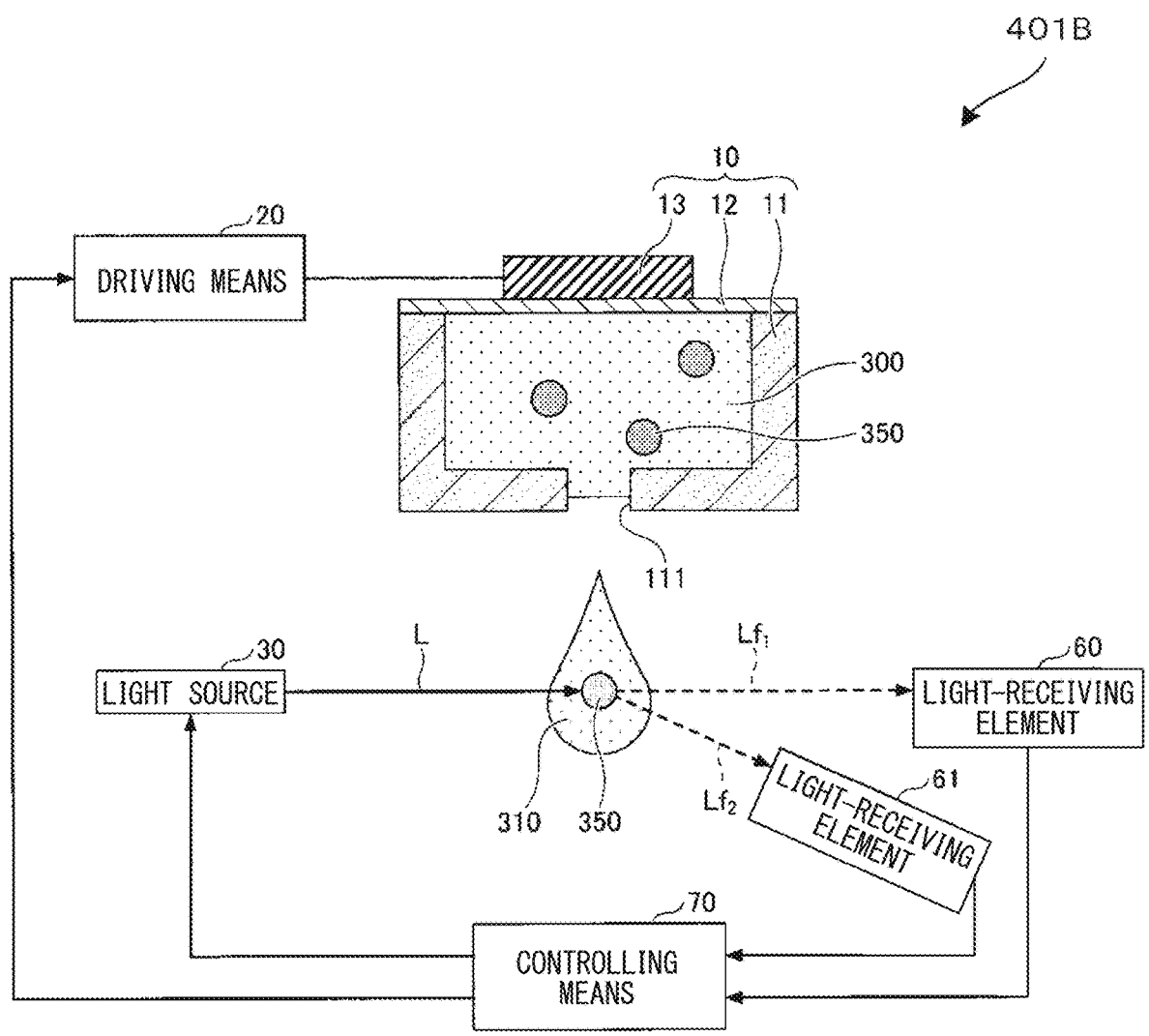
FIG. 15 is a schematic view showing another modified example of the liquid droplet-forming device.

The method for optically detecting will be described below with reference to FIGS. 10, 14, and 15. FIG. 10 is a schematic view showing one example of a liquid droplet-forming device 401. FIGS. 14 and 15 are schematic views showing other examples (401A and 401B) of a liquid droplet-forming device. As shown in FIG. 10, the liquid droplet-forming device 401 includes an ejection head (a liquid droplet-ejecting means) 10, a driving means 20, a light source 30, a light-receiving element 60, and a controlling means 70.

In FIG. 10, a liquid in which cells are fluorescently stained with a specific dye and then dispersed in a predetermined solution is used as a cell suspension, liquid droplets formed from an ejection head are irradiated with light having a specific wavelength, which is emitted from a light source, and the cells emit fluorescence that is detected by a light-receiving element, whereby the cells are counted. At this time, in addition to the method of staining cells with a fluorescent dye, autofluorescence emitted by a molecule originally contained in the cells may be used. Alternatively, a gene encoding a fluorescent protein (for example, green fluorescent protein (GFP)) may be introduced into cells in advance so that the cells emit fluorescence. Irradiating with light means shedding light.

An ejection head 10 has a liquid chamber 11, a membrane 12, and a driving element 13, and can eject, as the liquid droplet, a cell suspension 300 in which fluorescently stained cells 350 are suspended.

The liquid chamber 11 is a liquid-retaining part for retaining the cell suspension 300 in which the fluorescently stained cells 350 are suspended, and a nozzle 111 which is a through-hole is formed on the lower surface side. The liquid chamber 11 can be formed of, for example, metal, silicon, ceramics, or the like. Examples of the fluorescently stained cell 350 include an inorganic fine particle and an organic polymer particle stained with a fluorescent dye.

The membrane 12 is a film-like member fixed at the upper end part of the liquid chamber 11. The plane shape of the membrane 12 can be, for example, circular, but may be elliptical, quadrangular, or the like.

The driving element 13 is provided on the upper surface side of the membrane 12. The shape of the driving element 13 can be designed in accordance with the shape of the membrane 12. For example, in the case where the plane shape of the membrane 12 is circular, it is preferable to provide the driving element 13 having a circular shape.

The membrane 12 can be vibrated by supplying a driving signal from the driving means 20 to the driving element 13. In the case where the membrane 12 is vibrated, the liquid droplet 310 containing the fluorescently stained cells 350 can be ejected from the nozzle 111.

In the ease where a piezoelectric element is used as the driving element 13, for example, a structure can be provided in which electrodes for applying a voltage are provided on the upper surface and the lower surface of the piezoelectric material. In this case, in the case where a voltage is applied between the upper and lower electrodes of the piezoelectric element from the driving means 20, compressive stress is applied in the lateral direction of the paper surface, and thus a membrane 12 can be vibrated in the vertical direction of the paper surface. As the piezoelectric material, for example, lead zirconate titanate (PZT) can be used. In addition to the above, various piezoelectric materials such as bismuth iron oxide, metal niobate, barium titanate, and a material obtained by adding a metal or another oxide to these materials can be used.

The light source 30 irradiates a flying liquid droplet 310 with light L. The term "flying" means a state after the liquid droplet 310 is ejected from the liquid droplet-ejecting means 10 and until it lands on the landing target object. The flying liquid droplet 310 is substantially spherical at the position where the flying liquid droplet 310 is irradiated with the light L. In addition, the beam shape of the light L is substantially circular.

Here, it is preferable that the beam diameter of the light L be about 10 to 100 times the diameter of the liquid droplet 310. This is because the light source 30 reliably irradiates the liquid droplet 310 with the light L even in the case where the positions of the liquid droplets 310 are scattered.

However, it is preferable that the beam diameter of the light L not greatly exceed 100 times the diameter of the liquid droplet 310. This is because the energy density of the light with which the liquid droplet 310 is irradiated is decreased, the light quantity of fluorescence Lf emitted by using the light L as excitation light is decreased, and thus it is difficult for the light-receiving element 60 to detect the light.

The light L emitted from the light source 30 is preferably pulse light, and for example, a solid-state laser, a semiconductor laser, a dye laser, or the like is preferably used. In the case where the light L is pulse light, the pulse width is preferably 10 µs or less and more preferably 1 µs or less. The energy per unit pulse largely depends on the presence or absence of light collection or the like and the optical system but is generally preferably 0.1 µJ or more and more preferably 1 µJ or more.

In the case where the flying liquid droplet 310 contains the fluorescently stained cells 350, the light-receiving element 60 receives the fluorescence Lf emitted by the fluorescently stained cell 350 which absorbs the light L as excitation light. Since the fluorescence Lf is emitted from the fluorescently stained cell 350 in all directions, the light-receiving element 60 can be disposed at any position where the fluorescence Lf can be received. At this case, in order to improve the contrast, it is preferable to dispose the light-receiving element 60 at a position where the light L emitted from the light source 30 is not directly incident.

The light-receiving element 60 is not particularly limited as long as it is an element capable of receiving fluorescence Lf emitted from the fluorescently stained cell 350, and can be appropriately selected depending on the intended purpose; however, it is preferably an optical sensor that receives fluorescence from cells in the liquid droplet, which is emitted by irradiating the liquid droplet with light having a specific wavelength. Examples of the light-receiving element 60 include one-dimensional elements such as a photodiode and a photosensor, but, it is preferable to use a photomultiplier tube or an avalanche photodiode in the case where a highly sensitive measurement is required. As the light-receiving element 60, for example, a two-dimensional element such as a charge-coupled device (CCD), a complementary-metal-oxide semiconductor (CMOS), or a gate CCD may be used.

Since the fluorescence Lf emitted by the fluorescently stained cell 350 is weaker than the light L emitted by the light source 30, a filter for damping the wavelength range of the light L may be installed in the front stage (the light-receiving surface side) of the light-receiving element 60. As a result, in the light-receiving element 60, an image of the fluorescently stained cell 350 having a very high contrast can be obtained. As the filter, for example, a notch filter that damps a specific wavelength range including the wavelength of light L can be used.

Further, as described above, the light L emitted from the light source 30 is preferably pulse light, but the light L emitted from the light source 30 may be continuously oscillating light. In this case, it is preferable to control the light-receiving element 60 so that the light-receiving element 60 is capable of incorporating light at the timing at which the flying liquid droplet 310 is irradiated with the continuously oscillating light and cause the light-receiving element 60 to receive the fluorescence Lf.

The controlling means 70 has a function of controlling the driving means 20 and the light source 30. Further, the controlling means 70 has a function of obtaining information based on the light quantity received by the light-receiving element 60 and measuring the number of fluorescently stained cells 350 (the case where the number is zero is included) contained in the liquid droplet 310. Hereinafter, the operation of the liquid droplet-forming device 401 including the operation of the controlling means 70 will be described with reference to FIGS. 11 to 13.

Figure 11:
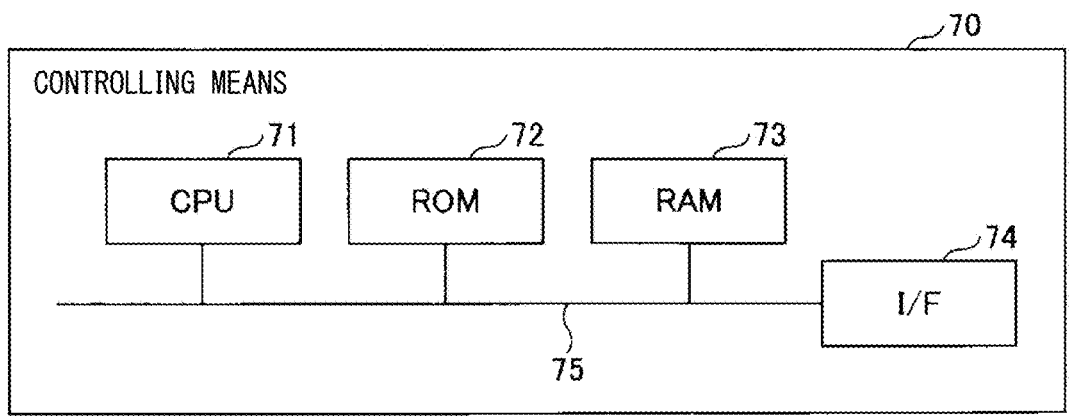
FIG. 11 is a view showing a hardware block of means for controlling the liquid droplet-forming device of FIG. 10.
Figure 12:
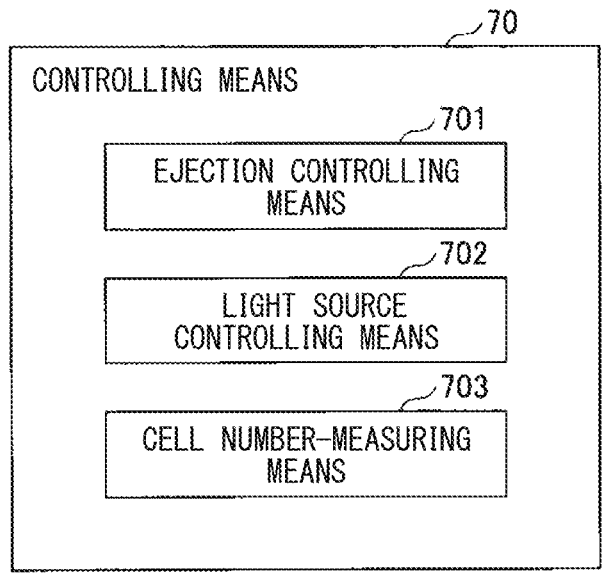
FIG. 12 is a view showing a functional block of means for controlling the liquid droplet-forming device of FIG. 10.
Figure 13:
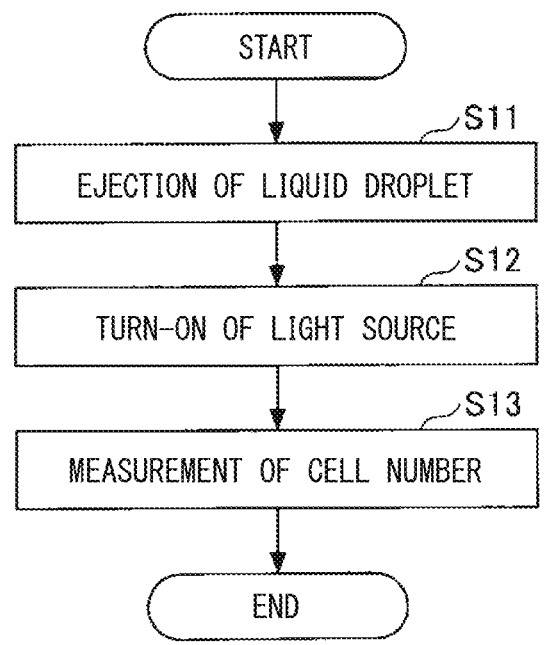
FIG. 13 is a flowchart showing one example of the operation of the liquid droplet-forming device.

FIG. 11 is a view showing a hardware block of means for controlling the liquid droplet-forming device of FIG. 10. FIG. 12 is a view showing a functional block of means for controlling the liquid droplet-forming device of FIG. 10. FIG. 13 is a flowchart showing one example of the operation of the liquid droplet-forming device.

As shown in FIG. 11, the controlling means 70 includes a CPU 71, a ROM 72, a RAM 73, a communication interface (a communication I/F) 74, and a bus line 75. The CPU 71, the ROM 72, the RAM 73, and the I/F 74 are connected to each other via a bus line 75.

The CPU 71 controls each of the functions of the controlling means 70. The ROM 72, which is a storing means, stores a program that is executed by the CPU 71 to control each of the functions of the controlling means 70 and various information. The RAM 73, which is a storing means, is used as a working area or the like of the CPU 71. In addition, the RAM 73 can temporarily store predetermined information. The I/F 74 is an interface for connecting the liquid droplet-forming device 401 to other devices or the like. The liquid droplet-forming device 401 may be connected to an external network or the like via the I/F 74.

As shown in FIG. 12, the controlling means 70 has, as a functional block, an ejection controlling means 701, a light source controlling means 702, and a cell number-measuring means (a cell number detecting means) 703.

The cell number-measuring of the liquid droplet-forming device 401 will be described with reference to FIGS. 12 and 13. First, in a step S11, the ejection controlling means 701 of the controlling means 70 sends an ejection command to the driving means 20. The driving means 20 that receives the ejection command from the ejection controlling means 701 supplies a driving signal to the driving element 13 to vibrate the membrane 12. Due to the vibration of the membrane 12, the liquid droplet 310 containing the fluorescently stained cells 350 is ejected from the nozzle 111.

Next, in a step S12, the light source controlling means 702 of the controlling means 70 sends a lighting command to the light source 30 in synchronization with the ejection of the liquid droplet 310 (in synchronization with the driving signal supplied from the driving means 20 to the liquid droplet-ejecting means 10). As a result, the light source 30 is turned on, and irradiate the flying liquid droplet 310 with the light L.

Here, the synchronization does not mean that the liquid droplet emits light at the same time as the liquid droplet 310 is ejected by the liquid droplet-ejecting means 10 (at the same time as the driving means 20 supplies the driving signal to the liquid droplet-ejecting means 10) but means that the light source 30 emits light at the timing at which the liquid droplet 310 is irradiated with the light L when the liquid droplet 310 flies and reaches a predetermined position. That is, the light source controlling means 702 controls the light source 30 so that the light is emitted with a delay of a predetermined time with respect to the ejection (the driving signal supplied from the driving means 20 to the liquid droplet-ejecting means 10) of the liquid droplet 310 by the liquid droplet-ejecting means 10.

For example, the velocity v of the liquid droplet 310 to be ejected when the driving signal is supplied to the liquid droplet-ejecting means 10 is measured in advance. Then, the time t required for reaching a predetermined position after the liquid droplet 310 is ejected is calculated based on the measured velocity v, and the light source 30 irradiates the light and the timing at which the light source emits light is delayed by t with respect to the timing at which the driving signal is supplied to the liquid droplet-ejecting means 10. As a result, good light emission control is possible, and the liquid droplet 310 can be reliably irradiated with the light from the light source 30.

Next, in a step S13, the cell number-measuring means 703 of the controlling means 70 measures the number of fluorescently stained cells 350 (the case where the number is zero is included) contained in the liquid droplet 310 based on the information from the light-receiving element 60. Here, the information from the light-receiving element 60 is a brightness value (a light quantity) or area value of the fluorescently stained cells 350.

The cell number-measuring means 703 can measure the number of fluorescently stained cells 350 by comparing, for example, the light quantity received by the light-receiving element 60 with a preset threshold value. In this case, a one-dimensional element or a two-dimensional element may be used as the light-receiving element 60.

In the case where a two-dimensional element is used as the light-receiving element 60, the cell number-measuring means 703 may perform image processing technique for calculating the brightness value or area of the fluorescently stained cells 350 based on the two-dimensional image obtained from the light-receiving element 60. In this case, the cell number-measuring means 703 can calculate the number of stained cells 350 by calculating the brightness values or area values of the fluorescently stained cells 350 by image processing or comparing the calculated brightness values or area values with a preset threshold value.

The fluorescently stained cell 350 may be a cell or a stained cell. The stained cell means a cell stained with a fluorescent dye or a cell capable of expressing a fluorescent protein. In the stained cells, the above-described fluorescent dye can be used. In addition, as the fluorescent protein, those described above can be used.

As described above, in the liquid droplet-forming device 401, the driving signal is supplied from the driving means 20 to the liquid droplet-ejecting means 10 retaining the cell suspension 300 in which the fluorescently stained cells 350 are suspended, the liquid droplet 310 containing the fluorescently stained cells 350 is ejected, and the flying liquid droplet 310 is irradiated with the light L from the light source 30. Then, the fluorescently stained cells 350 contained in the flying liquid droplet 310 emit fluorescence Lf using the light L as excitation light, and the light-receiving element 60 receives the fluorescence Lf. Further, based on the information from the light-receiving element 60, the cell number-measuring means 703 measures the number of (counts) fluorescently stained cells 350 contained in the flying liquid droplet 310.

That is, in the liquid droplet-forming device 401, since the number of fluorescently stained cells 350 contained in the flying liquid droplet 310 is actually observed on the spot, the measurement accuracy of the number of fluorescently stained cells 350 is improved as compared with the conventional case. Further, since the fluorescently stained cells 350 contained in the flying liquid droplets 310 are irradiated with the light L to emit the fluorescence Lf and then the fluorescence Lf is received by the light-receiving element 60, an image of the fluorescently stained cells 350 can be obtained with high contrast, whereby it is possible to reduce the frequency of occurrence of an erroneous measurement of the number of fluorescently stained cells 350.

FIG. 14 is a schematic view showing a modified example of the liquid droplet-forming device 401 of FIG. 10. As shown in FIG. 14, a liquid droplet-forming device 401A is different from the liquid droplet-forming device 401 (see FIG. 10) in that a mirror 40 is disposed in front of the light-receiving element 60. It is noted that the description for the same component as that of the embodiment described above may be omitted.

As described above, in the liquid droplet-forming device 401A, the degree of freedom in the layout of the light-receiving element 60 can be improved by disposing the mirror 40 in front of the light-receiving element 60.

For example, in the case where the nozzle 111 is brought to be close to the landing target object, interference may occur between the landing target object and the optical system (particularly, the light-receiving element 60) of the liquid droplet-forming device 401 in the layout of FIG. 10. However, in the case where the layout shown in FIG. 14 is adopted, it is possible to avoid the occurrence of interference.

In the case of changing the layout of the light-receiving element 60 as shown in FIG. 14, it is possible to reduce the distance (gap) between the landing target object on which the liquid droplet 310 lands and the nozzle 111, and thus the scattering of landing positions can be suppressed. As a result, it is possible to improve the accuracy of dispensing.

FIG. 15 is a schematic view showing another modified example of the liquid droplet-forming device 401 of FIG. 10. As shown in FIG. 15, the liquid droplet-forming device 401B is different from the liquid droplet-forming device 401 (see FIG. 10) in that a light-receiving element 61 that receives fluorescence $Lf_2$ emitted from the fluorescently stained cell 350 is provided in addition to the light-receiving element 60 that receives the fluorescence $Lf_1$ emitted from the fluorescently stained cell 350. It is noted that the description for the same component as that of the embodiment described above may be omitted.

Here, the fluorescence $Lf_1$ and $Lf_2$ indicate a part of the fluorescence emitted from the fluorescently stained cell 350 in all directions. The light-receiving elements 60 and 61 can be disposed at any positions at which the fluorescence emitted from the fluorescently stained cell 350 in different directions can be received. It is noted that three or more light-receiving elements may be disposed at positions at which the fluorescence emitted from the fluorescently stained cell 350 in different directions can be received. Further, each of the light-receiving elements may have the same specification or may have different specifications different from each other.

In the case where there is only one light-receiving element, there is a risk that the cell number-measuring means 703 will erroneously measure the number of (erroneously count) fluorescently stained cells 350 contained in the liquid droplet 310 due to the overlapping of the fluorescently stained cells 350, in the case where the flying liquid droplet 310 contains a plurality of fluorescently stained cells 350.

Figure 16A:
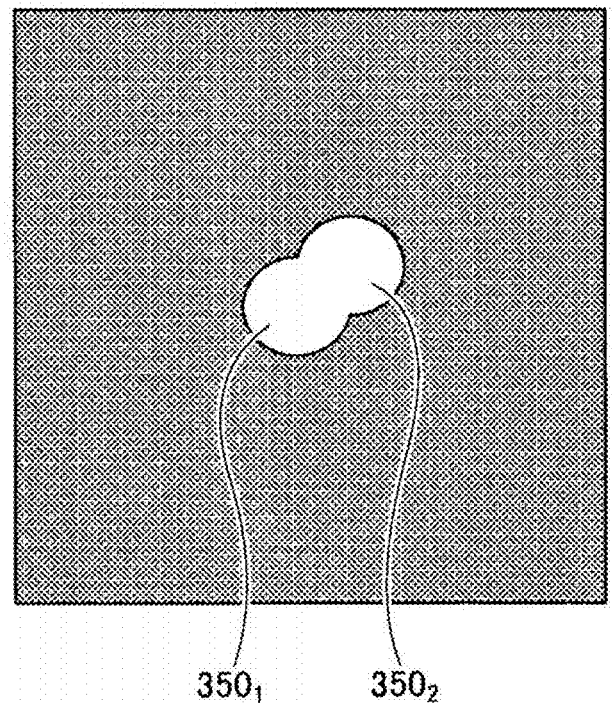
FIGS. 16 (a) and (b) are views showing a case where flying liquid droplets contain two fluorescent particles.
Figure 16B:
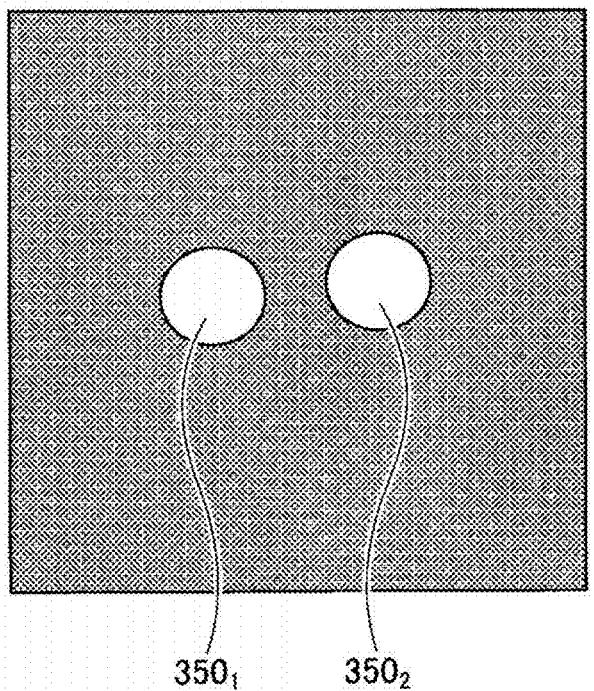

FIG. 16 (*a*) and FIG. 16 (*b*) are views showing a case where a flying liquid droplet contains two fluorescently stained cells. For example, there may be a case where the fluorescently stained cells 350*a* and 350*b* overlap, as shown in FIG. 16 (*a*), or a case where the fluorescently stained cells 350*a* and 350*b* do not overlap, as shown in FIG. 16 (*b*). In the case where two or more light-receiving elements are provided, it is possible to reduce the influence of overlapping of fluorescently stained cells.

As described above, the cell number-measuring means 703 can calculate the number of fluorescent particles by calculating the brightness values or area values of the fluorescent particles by image processing and comparing the calculated brightness values or area values with a preset threshold value.

In the case where two or more light-receiving elements are installed, it is possible to suppress the occurrence of a counting error by adopting data indicating the maximum value among the brightness values or area values obtained from each of the light-receiving elements. This will be described in more detail with reference to FIG. 17.

Figure 17:
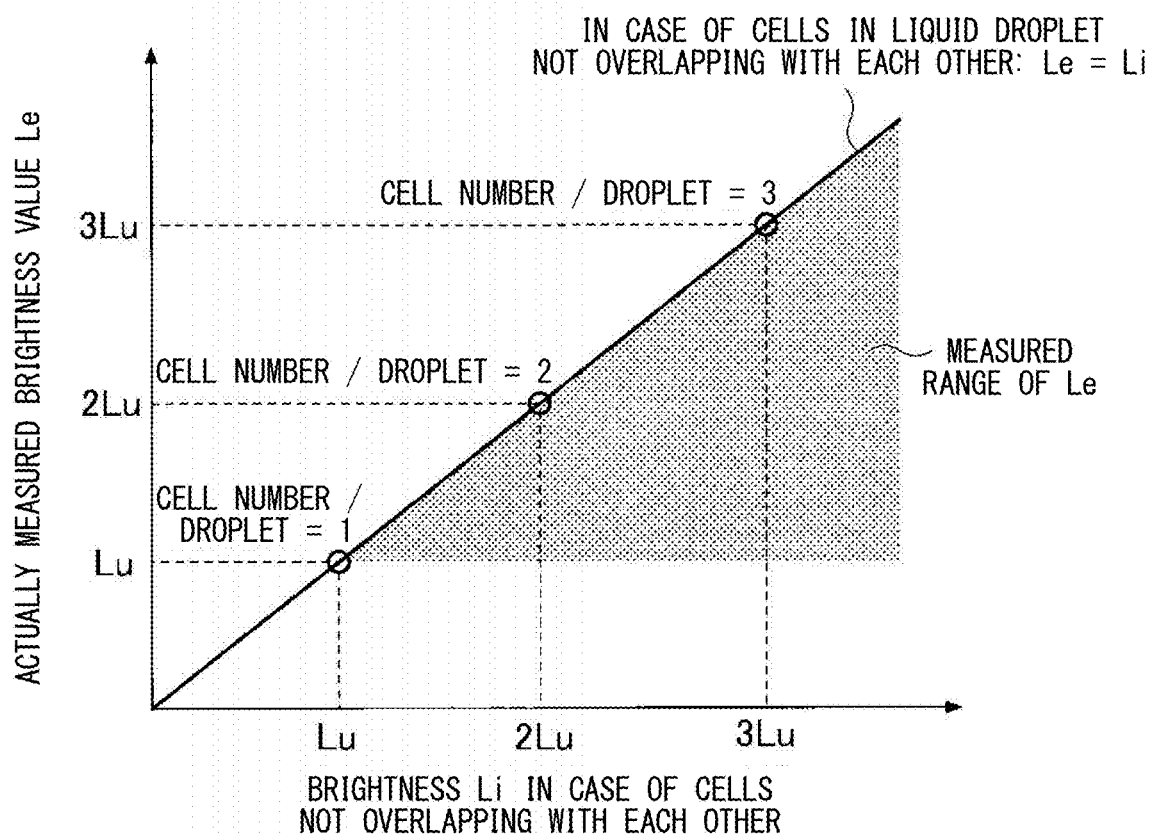
FIG. 17 is a view showing the relationship between a brightness value Li in the case where particles do not overlap with each other and an actually measured brightness value Le.

FIG. 17 is a view showing the relationship between a brightness value Li in the case where particles do not overlap with each other and an actually measured brightness value Le. As shown in FIG. 17, in the case where there is no overlap between the particles in the liquid droplet, an expression Le=Li holds. For example, in the case where the brightness value of one cell is denoted by Lu, an expression Le=Lu holds in the case where the number of cells per drop is 1, and an expression Le=n Lu holds in the case where the number of cells per drop is n (n: natural number).

However, in reality, in the case where n is 2 or more, particles may overlap with each other, and thus the actually measured brightness value Le is, Lu≤Le≤n Lu (corresponding to the shaded portion in FIG. 17). Accordingly, in the case where the number of cells per drop is n, the threshold value can be set as, for example, (n Lu−Lu/2)≤threshold value<(n Lu+Lu/2). In the case where a plurality of light-receiving elements are installed, it is possible to suppress the occurrence of a counting error by adopting data indicating the maximum value among the data obtained from each of the light-receiving elements. The area value may be used instead of the brightness value.

Further, in the case where a plurality of light-receiving elements are installed, the number of cells may be determined by an algorithm for estimating the number of cells based on the obtained plurality of shape data. As described above, since the liquid droplet-forming device 401B has a plurality of light-receiving elements that receive the fluorescence emitted from the fluorescently stained cells 350 in different directions, the frequency of occurrence of an erroneous measurement of the number of fluorescently stained cells 350 can be further reduced.

Figure 18:
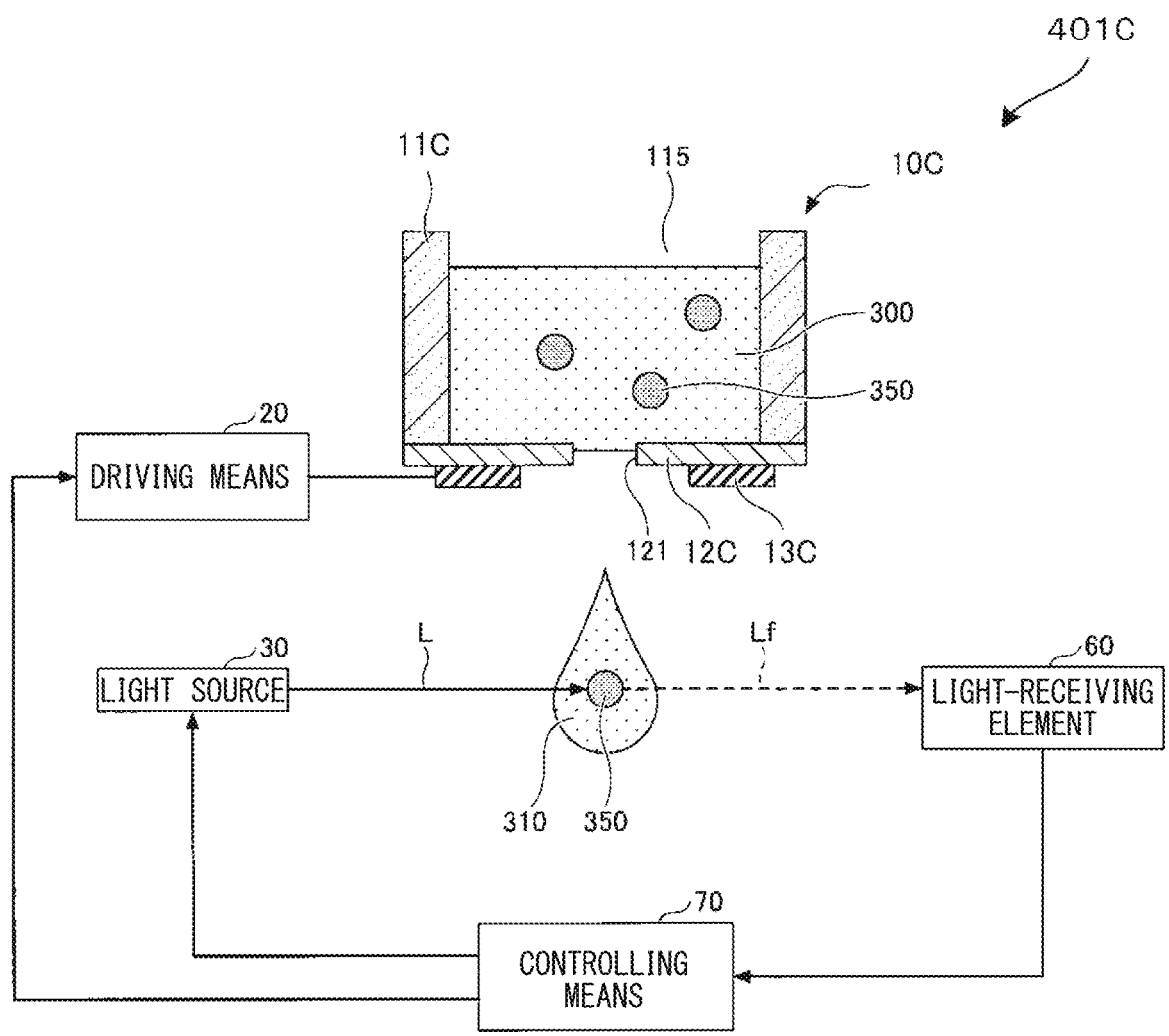
FIG. 18 is a schematic view showing another modified example of the liquid droplet-forming device.

FIG. 18 is a schematic view showing another modified example of the liquid droplet-forming device 401 of FIG. 10. As shown in FIG. 18, a liquid droplet-forming device 401C is different from the liquid droplet-forming device 401 (see FIG. 10) in that the liquid droplet-ejecting means 10 is replaced with a liquid droplet-ejecting means 10C. It is noted that the description for the same component as that of the embodiment described above may be omitted.

The liquid droplet-ejecting means 10C has a liquid chamber 11C, a membrane 12C, and a driving element 13C. The liquid chamber 11C has, at the upper part thereof, an atmospheric air opening part 115 that opens the inside of the liquid chamber 11C to the atmosphere and is configured so that air bubbles mixed in the cell suspension 300 can be discharged from the atmospheric air opening part 115.

The membrane 12C is a film-like member fixed at the lower end part of the liquid chamber 11C. A nozzle 121, which is a through-hole, is formed at the substantial center of the membrane 12C, and the cell suspension 300 retained in the liquid chamber 11C is ejected as the liquid droplet 310 from the nozzle 121 by the vibration of the membrane 12C. Since the liquid droplet 310 is formed by the inertia of the vibration of the membrane 12C, even the cell suspension 300 having a high surface tension (a high viscosity) can be ejected. The plane shape of the membrane 12C can be, for example, circular, but may be elliptical, quadrangular, or the like.

The material of the membrane 12C is not particularly limited, but in the case where the material is too soft, the membrane 12C vibrates easily, and thus it is difficult to immediately suppress the vibration when performing ejection. Accordingly, it is preferable to use a material having a predetermined degree of hardness. As the material of the membrane 12C, for example, a metal material, a ceramic material, a polymer material having a certain a predetermined degree of hardness, or the like can be used.

In particular, in the case where cells are used as fluorescently stained cells 350, it is preferable that the material have low attachability to a cell and a protein. It is generally said that the attachability of a cell depends on the contact angle of water on the material, and in the case where the material has low hydrophilicity or high hydrophobicity, the cell attachability is low. Various metal materials and ceramics (metal oxides) can be used as the material having high hydrophilicity, and a fluorescein or the like can be used as the material having high hydrophobicity.

Other examples of such materials include stainless steel, nickel, aluminum and the like, silicon dioxide, alumina, and zirconia. Apart from the above, it is also conceivable to reduce cell adhesiveness by coating the surface of the material. For example, the surface of the material can be coated with the above-described metal or metal oxide material, or with a synthetic phospholipid polymer mimicking a cell membrane (for example, Lipidure manufactured by NOF Corporation).

It is preferable that the nozzle 121 be formed as a substantially circular through-hole at the substantial center of the membrane 12C. In this case, the diameter of the nozzle 121 is not particularly limited, but it is preferably at least two times the size of the fluorescently stained cells 350 in order to prevent the nozzle 121 from being clogged by the fluorescently stained cells 350. In the case where the fluorescently stained cell 350 is, for example, an animal cell, particularly a human cell, since the size of the human cell is generally about 5 μm to 50 μm, the diameter of the nozzle 121 is preferably 10 μm or more and more preferably 100 μm or more in accordance with the cell to be used.

On the other hand, in the case where the liquid droplet is too large, it is difficult to achieve the purpose of forming a fine liquid droplet, and thus the diameter of the nozzle 121 is preferably 200 μm or less. That is, in the liquid droplet-ejecting means 10C, the diameter of the nozzle 121 is typically in the range of 10 μm or more and 200 μm or less.

The driving element 13C is formed on the lower surface side of the membrane 12C. The shape of the driving element 13C can be designed in accordance with the shape of the membrane 12C. For example, in the case where the plane shape of the membrane 12C is circular, it is preferable to form a driving element 13C having the plane shape of an annular shape (a ring shape) around the nozzle 121. The driving system of the driving element 13C can be the same as that of the driving element 13.

The driving means 20 can selectively (for example, alternately) apply an ejection wave form for vibrating the membrane 12C to form the liquid droplet 310 and a stirring wave form for vibrating the membrane 12C within a range that does not form the liquid droplet 310 to the driving element 13C.

For example, in the case of making both the ejection wave form and the stirring wave form a rectangular wave and lowering the driving voltage of the stirring wave form in comparison with the driving voltage of the ejection wave form, it is possible to prevent the liquid droplet 310 from being formed by applying the stirring wave form. That is, the vibration state (the degree of vibration) of the membrane 12C can be controlled by the level of the driving voltage.

In the liquid droplet-ejecting means 10C, since the driving element 13C is formed on the lower surface side of the membrane 12C, in the case where the membrane 12 vibrates due to the driving element 13C, a flow from the lower side to the upper side of the liquid chamber 11C can be generated.

In this case, the movement of the fluorescently stained cell 350 is a movement from the bottom side to the top side, and convection occurs in the liquid chamber 11C, whereby the cell suspension 300 containing the fluorescently stained cells 350 is stirred. Due to the flow from the lower side to the upper side of the liquid chamber 11C, the sedimented and aggregated fluorescently stained cells 350 are uniformly dispersed inside the liquid chamber 11C.

That is, the driving means 20 applies the ejection wave form to the driving element 13C and controls the vibration state of the membrane 12C, and thus the cell suspension 300 retained in the liquid chamber 11C can be ejected from the nozzle 121 as the liquid droplet 310. In addition, the driving means 20 applies the stirring wave form to the driving element 13C and controls the vibration state of the membrane 12C, and thus the cell suspension 300 retained in the liquid chamber 11C can be stirred. At the time of stirring, the liquid droplet 310 is not ejected from the nozzle 121.

In the case where the cell suspension 300 is stirred in this manner while the liquid droplets 310 are not formed, it is possible to prevent the fluorescently stained cells 350 from sedimenting and aggregating on the membrane 12C and is possible to uniformly disperse the fluorescently stained cells 350 in the cell suspension 300. As a result, it is possible to suppress the clogging of the nozzle 121 and the scattering of the numbers of fluorescently stained cells 350 in the ejected liquid droplet 310. As a result, the cell suspension 300 containing the fluorescently stained cells 350 can be continuously and stably ejected as liquid droplets 310 for a long period of time.

Further, in the liquid droplet-forming device 401C, air bubbles may be mixed in the cell suspension 300 in the liquid chamber 11C. Even in this case, in the liquid droplet-forming device 401C, since the atmospheric air opening part 115 is provided at the upper part of the liquid chamber 11C, the air bubbles mixed in the cell suspension 300 can be discharged to the outside atmospheric air through the atmospheric air opening part 115. As a result, it is possible to continuously and stably form the liquid droplets 310 without consuming a large amount of liquid for discharging air bubbles.

That is, in the case where air bubbles are mixed in the vicinity of the nozzle 121 or in the case where a large number of air bubbles are mixed in the membrane 12C, the ejection state is affected. Therefore, in order to stably form the liquid droplets for a long period of time, it is necessary to discharge the mixed air bubbles. Typically, the air bubbles mixed in the membrane 12C move upward naturally or by the vibration of the membrane 12C. However, since the atmospheric air opening part 115 is provided in the liquid chamber 11C, the mixed air bubbles can be discharged through the atmospheric air opening part 115. Therefore, even in the case where air bubbles are mixed in the liquid chamber 11C, it is possible to prevent non-ejection from occurring, and the liquid droplet 310 can be continuously and stably formed.

At the timing at which the liquid droplets are not formed, the membrane 12C may be vibrated within a range where the liquid droplets are not formed so that the air bubbles are actively moved to the upside of the liquid chamber 11C.

(Method for Electrical or Magnetic Detecting)

Figure 19:
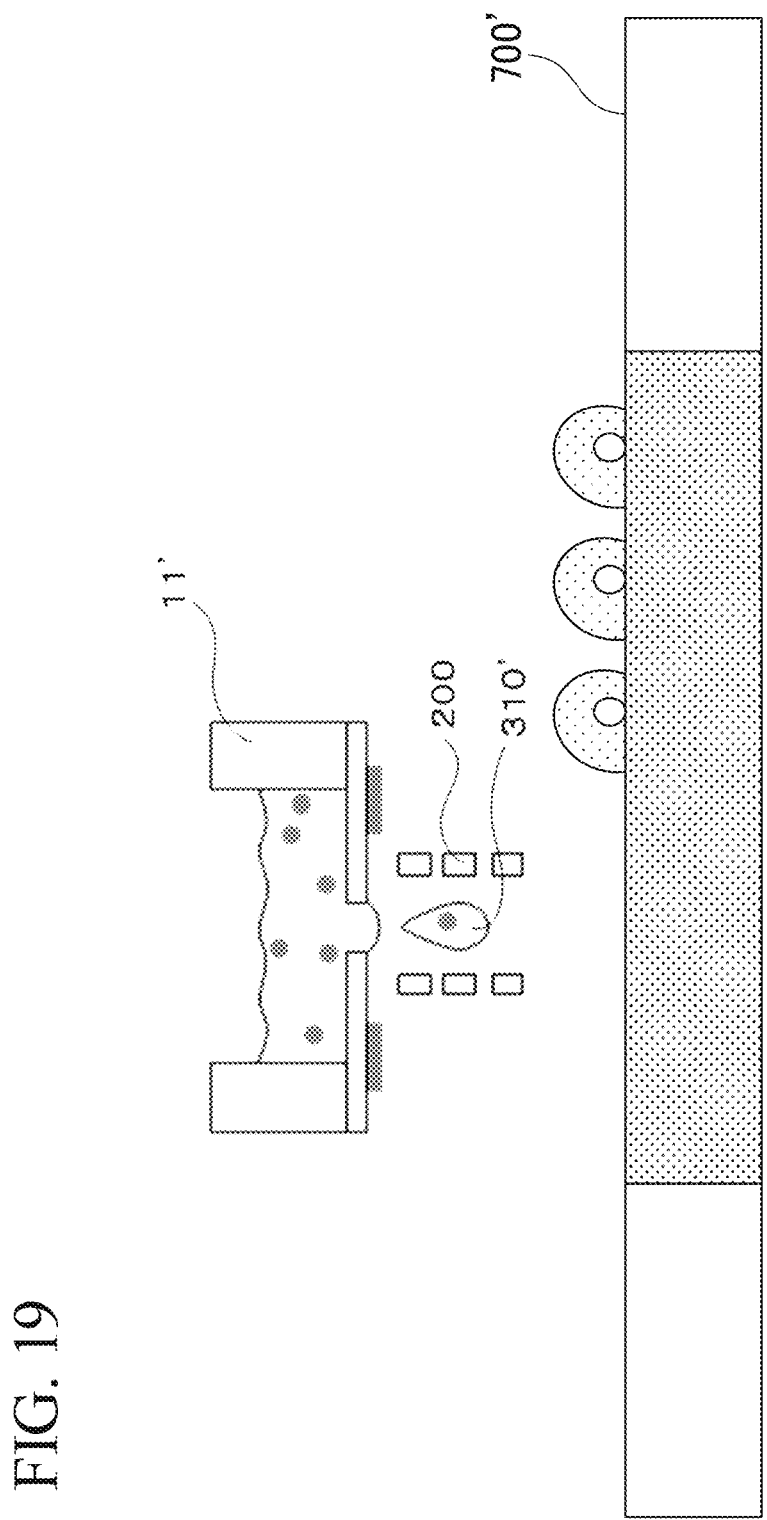
FIG. 19 is a schematic view showing another example of a liquid droplet-forming device.

For the method for electrical or magnetic detecting, as shown in FIG. 19, a coil 200 for measuring the number of cells is installed as a sensor directly under an ejection head that ejects a cell suspension as liquid droplets 310' from a liquid chamber 11' to a base material 700'. In the case where cells are covered with magnetic beads that have been modified by a specific protein and capable of adhering to the cells, it is possible to detect the presence or absence of the cells in the flying liquid droplet due to the induced current that is generated as the cells to which magnetic beads are attached pass through the coil. Generally, a cell has a protein peculiar to the cell on the surface thereof, and thus it is possible to attach a magnetic bead to the cell by modifying the magnetic bead with an antibody capable of adhering to the protein. A ready-made product can be used as such magnetic beads, and for example, Dynabeads (registered trade mark) manufactured by VERITAS Corporation can be used.

(Treatment for Observing Cells Before Ejection)

Figure 20:
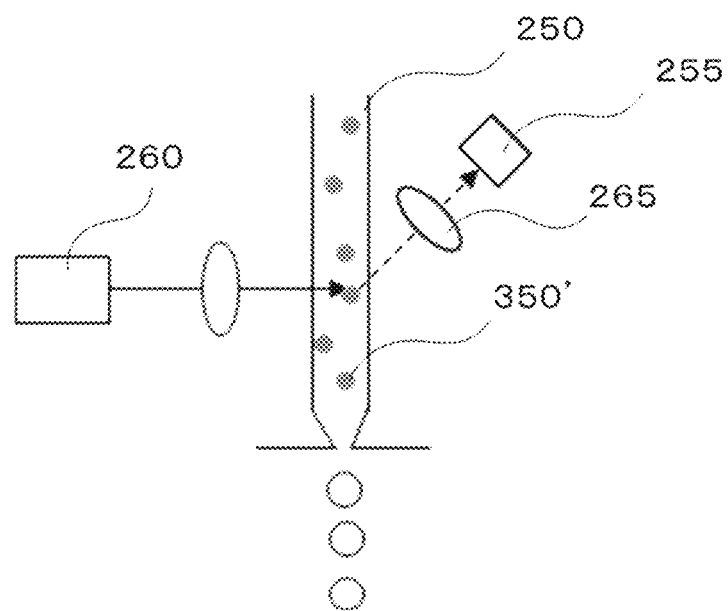
FIG. 20 is a schematic view showing one example of a method for counting cells that have passed through a micro flow path.
Figure 21:
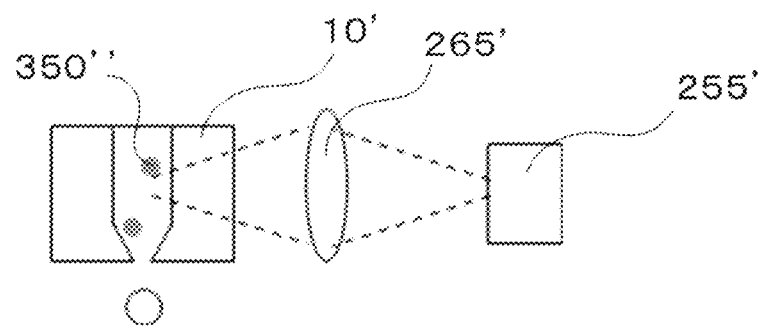
FIG. 21 is a schematic view showing one example of a method for acquiring an image of the vicinity of a nozzle part of an ejection head.

Examples of the treatment for observing cells before ejection include a method for counting cells 350' which have passed through a micro flow path 250 shown in FIG. 20 and a method for acquiring an image of the vicinity of the nozzle part of the ejection head shown in FIG. 21.

The method shown in FIG. 20 is a method used in a cell sorter apparatus, and for example, a cell sorter SH800Z manufactured by Sony Corporation can be used. In FIG. 20, it is possible to form liquid droplets while identifying the presence or absence of cells and the kinds of cells by irradiating the micro flow path 250 with laser light from a light source 260 and detecting scattered light or fluorescence with a detector 255 using a condenser lens 265. In the case where this method is used, it is possible to estimate the number of cells that have landed in the predetermined well from the number of cells that have passed through the micro flow path 250.

Further, as the ejection head 10' shown in FIG. 21, a single cell printer manufactured by Cytena Gmbh can be used. In FIG. 21, it is possible to estimate the number of cells that landed in the predetermined well by estimating that the cells 350" in the vicinity of the nozzle part have been ejected based on the result obtained by analyzing an image of the vicinity of the nozzle part, where the image is acquired by an image acquisition part 255' through a lens 265' before ejection, or by estimating the number of cells that are considered to have been ejected based on the difference in cell number between images before and after the ejection. In the method for counting cells that have passed through the micro flow path, which is shown in FIG. 20, liquid droplets are continuously generated, whereas, in FIG. 21, liquid droplets can be formed on demand, which is more preferable.

(Treatment for Counting Cells after Landing)

As the treatment for counting cells after landing, it is possible to adopt a method for detecting fluorescently stained cells by observing wells on the plate with a fluorescence microscope or the like, Such a method is described, for example, in Moon S., et al., Drop-on-demand single cell isolation and total RNA analysis, PLoS One, Vol. 6, Issue 3, e17455, 2011.

The method for observing cells before the ejection of the liquid droplet and after the landing of the liquid droplet has the following problems, and thus it is most preferable to observe cells that are being ejected in the liquid droplet, depending on the kind of base material to be generated.

In the method for observing cells before ejection, the number of cells that are considered to have landed is measured based on the number of cells that have passed through the flow path and the observation of the images before and after ejection, and thus it is not checked whether the cells have been actually ejected, whereby an unexpected error may occur. For example, in the case where the nozzle part is dirty, the liquid droplets are not ejected correctly and are attached to the nozzle plate, and thus the cells in the liquid droplet do not land. In addition, there may occur problems such as cells remaining in a narrow region of the nozzle part and cells moving more distantly than expected due to the ejection operation and moving out of the observation range.

There is also a problem in the method for detecting cells on the base material after landing. First, it is necessary to prepare a base material with which microscopic observation can be performed. As the base material with which observation can be performed, a base material having a transparent and flat bottom surface, particularly a base material having a glass bottom surface is generally used. However, since such base materials are special base materials, there is a problem in that a supporting part made of a general water-decomposable material can not be used. In addition, in the case where the number of cells is as large as several tens, there is a problem in that accurate counting cannot be performed because cells overlap.

Therefore, after ejecting the liquid droplet and before landing on the well of the liquid droplet, it is preferable to perform a treatment for observing cells before ejection and a treatment for counting the cells after landing, in addition to measuring the number of cells contained in the liquid droplet by a sensor and a cell number-measuring means.

As the light-receiving element, a light-receiving element having one or a small number of light-receiving parts, for example, a photodiode, an avalanche photodiode, a photomultiplier tube can be used. In addition, it is also possible to use a sensor such as a charge-coupled device (CCD), a complementary-metal-oxide semiconductor (CMOS), or a gate CCD, in which light-receiving elements are arranged two-dimensionally.

In the case where a light-receiving element having one or a small number of light-receiving parts is used, it is conceivable to determine how many cells are contained based on the fluorescence intensity by using a calibration curve prepared in advance.

However, binary detection of the presence or absence of cells in the flying liquid droplet is mainly performed. In the case where the cell concentration of the cell suspension is sufficiently low and only 1 or 0 cells are contained in the liquid droplets, it is possible to perform counting with sufficient accuracy by binary detection.

In the case of assuming that cells are randomly arranged in the cell suspension, the number of cells in the flying liquid droplet is considered to follow the Poisson distribution, and the probability P (>2) that two or more cells will be contained in the liquid droplet is represented by Expression 4 below.

$$P(>2)=1-(1+\lambda) \times e^{-\lambda} \qquad \text{Expression 4}$$

Figure 22:
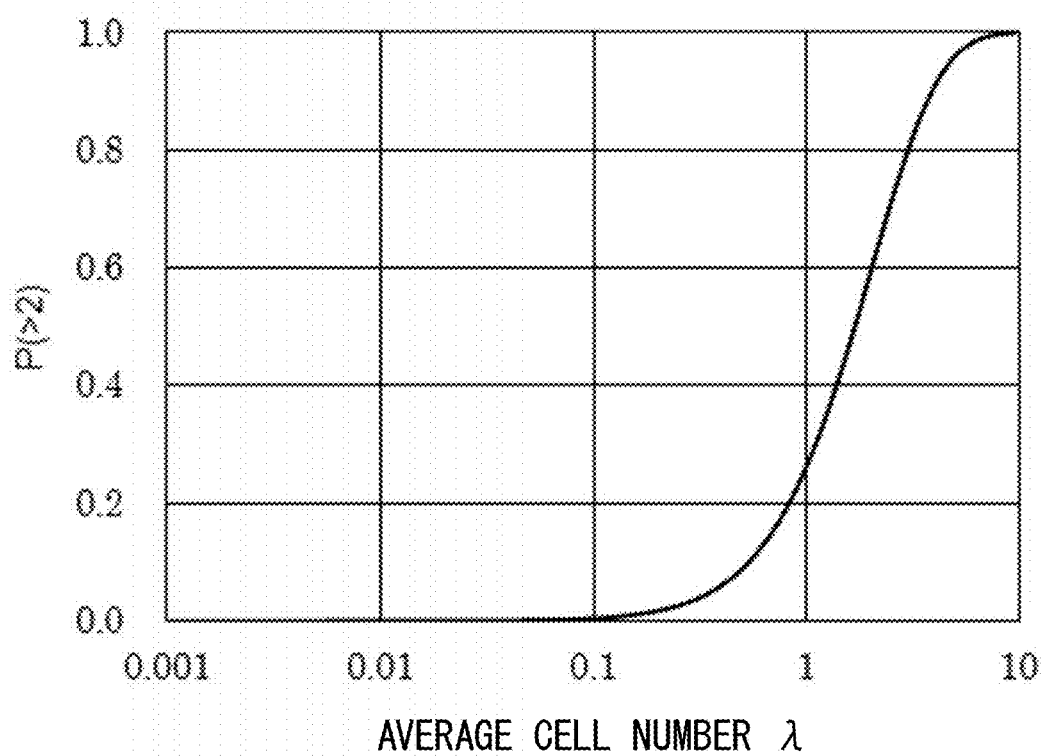
FIG. 22 is a graph showing the relationship between the probability P (>2) and the average cell number.

FIG. 22 is a graph showing the relationship between the probability P (>2) and the average cell number. Here, λ is the average cell number in the liquid droplet, which is obtained by multiplying the cell concentration in the cell suspension by the volume of the ejected liquid droplet.

In the case of measuring the number of cells by binary detection, it is preferable that the probability P (>2) be a sufficiently small value in order to ensure accuracy, and $\lambda<0.15$ is preferable, where the probability P (>2) is 1% or less. The light source is not particularly limited as long as it can induce the excitation of fluorescence of cells, and can be appropriately selected depending on the intended purpose. A light source in which a general lamp such as a mercury lamp or halogen lamp is equipped with a filter for emitting a specific wavelength, a light-emitting diode (LED), a laser, or the like can be used. However, it is preferable to use a laser since it is necessary to irradiate a narrow region with light having high intensity, particularly in the case of forming a fine liquid droplet of 1 nL or less. As the laser light source, various generally known lasers such as a solid-state laser, a gas laser, and a semiconductor laser can be used. Further, the excitation light source may be one that continuously emits light to the region through which the liquid droplet passes or may be one that emits light in a pulsed manner at a timing at which a predetermined time delay is applied to the liquid droplet ejection operation in synchronization with the liquid droplet ejection.

[Process of Calculating Certainty of Number of Molecules of Nucleic Acid Estimated in Cell Suspension Generation Process, Nucleic Acid Filling Process, and Cell Number-Measuring Process]

This process is a process of calculating the certainty in each of the nucleic acid-supporting process and the cell number-measuring process. The calculation of the certainty of the estimated copy number of the nucleic acid can be calculated in the same manner as the certainty in the cell suspension generation process.

Regarding the timing of the certainty calculation, the certainty may be collectively calculated in the next process of the cell number-measuring process or may be calculated by synthesizing each uncertainty in the next process of the cell number-measuring process, where each uncertainty is calculated at the end of each of the cell suspension generation process, the nucleic acid-supporting process, and the cell number-measuring process and then the certainty. In other words, the certainty in each of the above processes may be appropriately calculated before the synthetic calculation.

[Output Process]

The output process is a process of outputting the value measured by the cell number-measuring means based on the detection result measured by the sensor as the number of cells contained in the cell suspension landed on the base material. The to measured value means the number of cells contained in the container, which is measured by the cell number-measuring means from the detection result measured by the sensor.

Output means that a device such as a motor, a communication device, or a computing machine receives an input and transmits the measured value as electronic information to an external server as a counting result storing means, or prints the measured value as a printed matter.

In the output process, in the case where the base material is generated, the number of cells or the number of nucleic acids in the supporting part of the base material is observed or estimated, and the observed value or the estimated value is output to an external storage unit. The output may be performed at the same time as the cell number-measuring process is performed or may be performed after the cell number-measuring process.

[Recording Process]

The recording process is a process of recording the observed output value or estimated value in the output process. The recording process can be preferably carried out in the recording unit. The recording may be performed at the same time as the output process is performed or after the output process. The recording includes not only adding information to a recording medium but also storing information in a recording unit. In this case, the recording unit can be referred to as a storage unit.

[Other Process]

Other processes are not particularly limited, and can be appropriately selected depending on the intended purpose. Examples thereof include an enzyme deactivation process.

The enzyme deactivation process is a process of deactivating an enzyme. Examples of the enzyme include DNase and RNase. The method for deactivating an enzyme is not particularly limited and can be appropriately selected depending on the intended purpose, and a conventionally known method can be preferably used.

<Testing Method>

The testing method of the present embodiment is a method for testing the accuracy of a measurement value of a detection target gene in a cell sample, where the measurement value is obtained from a genetic testing apparatus, which includes using a carrier including a supporting part on which a specific number of cells A are supported, the cell A containing a specific number of copies of a nucleic acid.

As the carrier used in the testing method of the present embodiment, a plate having a supporting part on which a specific number of cells A containing a specific number of copies of a nucleic acid are supported can be used in addition to the same carrier as that exemplified in the section of <Carrier> described above.

The plate is not particularly limited, and a plate in which a well (or wells) is formed, which is generally used in the biotechnology field, can be used. That is, the supporting part in the plate can be rephrased as a well. The number of wells in the plate is not particularly limited, and can be appropriately selected depending on the intended purpose. The plate may have one well or a plurality of wells. Specifically, as the plate, it is preferable to use a 1-well microtube, an 8-well tube, a 96-well, a 384-well plate, or the like. In the case where a plurality of wells are used, the same number of cells can be applied or different numbers of cells can be added to the wells of these plates. In addition, there may be wells containing no cells.

Regarding a method for supporting cells on a plate, that is, a method for applying cells on a plate, cells can be supported by a method using a conventionally known inkjet technique, and specifically, for example, the method disclosed in Japanese Patent No. 6446151 can be used.

Details of the testing method of the present embodiment will be described below.

First Embodiment

The testing method of the present embodiment includes a process (an extraction efficiency calculation process) of calculating the extraction efficiency of the nucleic acid from the cell A using the carrier.

In addition to the above process, the testing method of the present embodiment preferably further includes a process (a determination process A) of determining the accuracy of the measurement value of the gene by a genetic testing apparatus from the extraction efficiency.

[Extraction Efficiency Calculation Process]

In the extraction efficiency calculation process, first, a nucleic acid is extracted from cell A using a carrier. Then, quantitative PCR is performed using the obtained nucleic acid to quantify the copy number of the nucleic acid. Next, the value obtained by dividing the quantification value by the known copy number of the nucleic acid present on the base material is calculated in terms of percentage as the extraction efficiency of the nucleic acid.

Extraction means destroying a cell membrane, a cell wall, or the like, and extracting a nucleic acid. As a method for extracting a nucleic acid from the cell A, a method of heat-treating at 90° C. or higher and 100° C. or lower is known. In the case of being heat-treated at 90° C. or lower, DNA may not be extracted, and in the case of being heat-treated at 100° C. or higher, DNA may be degraded. It is preferable to add a surfactant in the heat treatment.

The surfactant is not particularly limited, and can be appropriately selected depending on the intended purpose. Examples thereof include an ionic surfactant and a nonionic surfactant. One kind thereof may be used singly, or two or more kinds thereof may be used in combination. Among these, a nonionic surfactant is preferable since a protein is not denatured and is deactivated, which depends on the amount added though.

Examples of the ionic surfactant include fatty acid sodium, fatty acid potassium, alpha sulfo fatty acid ester sodium, sodium linear alkylbenzene sulfonate, alkyl sulfate ester sodium, alkyl ether sulfate ester sodium, and sodium alpha olefin sulfonate. One kind thereof may be used singly, or two or more kinds thereof may be used in combination. Of them, sodium fatty acid is preferable, and sodium dodecyl sulfate (SDS) is more preferable.

Examples of the nonionic surfactant include an alkyl glycoside, an alkyl polyoxyethylene ether (Brij series or the like), octylphenol ethoxylate (Triton X series, Igepal CA series, Nonidet P series, Nikkol OP series, or the like), polysorbates (Tween series such as Tween 20), sorbitan fatty acid ester, polyoxyethylene fatty acid ester, an alkyl maltoside, sucrose fatty acid ester, glycoside fatty acid ester, glycerin fatty acid ester, propylene glycol fatty acid ester, and fatty acid monoglyceride. One kind thereof may be used singly, or two or more kinds thereof may be used in combination. Among them, polysorbates are preferable.

The content of the surfactant is preferably 0.01% by mass or more and 5.00% by mass or less with respect to the total amount of the cell suspension in the well. In the case where the content is 0.01% by mass or more, the surfactant can exhibit an effect on DNA extraction, and in the case where the content is 5.00% by mass or less, the inhibition of amplification during PCR can be prevented. For this reason, the content is suitably 0.01% by mass or more and 5.00% by mass or less as the numerical range in which both effects described above can be obtained.

In the case of cells that have a cell wall, DNA may not be sufficiently extracted by the above method. Examples of the method for the above case include an osmotic shock method, a freeze-thaw method, an enzyme digestion method, the use of a DNA extraction kit, a sonication method, a French press method, and a method of using a homogenizer. Among them, an enzyme digestion method is preferable since the loss of the extracted DNA is small.

After destroying the cell membrane, the cell wall, or the like using the method described above, the nucleic acid can be purified from the cell extract solution using a conventionally known method. Nucleic acid purification can be performed by, for example, phenol extraction, chromatography, ion exchange, gel electrophoresis, density-dependent centrifugation, capturing with magnetic beads, and silica membrane method.

[Determination Process A]

In the determination process A, the accuracy of a measurement value of a detection target gene in a cell sample, where the measurement value is obtained from a genetic testing apparatus, is determined from the extraction efficiency calculated in the extraction efficiency calculation process.

Specifically, in the case where the extraction efficiency of the nucleic acid in the carrier is 80% or more, preferably 85% or more, more preferably 90% or more, still more preferably 95% or more, particularly preferably 99% or more, and most preferably 100%, it is determined that the measurement value of the detection target gene by the genetic testing apparatus may be accurate. On the other hand, in the case where the extraction efficiency of the nucleic acid in the carrier is less than 80%, it is determined that the measurement value of the detection target gene by the genetic testing apparatus may not be accurate.

Further, in the determination process A, the extraction efficiency of the nucleic acid in the carrier can be regarded as an estimated value of the extraction efficiency of the detection target gene.

Second Embodiment

In the case where the genetic testing apparatus is a quantitative PCR apparatus, the testing method of the present embodiment include a process (an extraction efficiency calculation process) of calculating the extraction efficiency of the nucleic acid from the cell A using the carrier; a process of amplifying the nucleic acid with a quantitative PCR apparatus by using two or more carriers respectively having different total copy numbers of nucleic acids contained in the carrier, creating a calibration curve, and then calculating the amplification efficiency (an amplification efficiency calculation process); and a process of determining the accuracy of the quantification value of the gene, where the quantification value is obtained with the quantitative PCR apparatus, from the extraction efficiency and the amplification efficiency (a determination process B).

In addition to the above process, the testing method of the present embodiment preferably further includes a process (a gene quantification process) of obtaining a quantification value of the detection target gene in the cell sample by a quantitative PCR apparatus.

Examples of the quantitative PCR apparatus include the same apparatus as that exemplified in the section of <Carrier> described above. The conditions for the quantitative PCR can be appropriately set depending on the nucleic acid to be amplified.

Since the extraction efficiency calculation process is the same as the process described in the section of <<First embodiment>>, the description thereof will be omitted.

[Amplification Efficiency Calculation Process]

In the amplification efficiency calculation process, a carrier is used to extract a nucleic acid from the cell supported on the supporting part of the carrier. The nucleic acid is amplified by the quantitative PCR using an extract containing the extracted nucleic acid. A calibration curve is created from the amplification result, and the amplification efficiency is calculated using the following expression.

$$\text{Amplification efficiency }(e) = 10^{(-1/\text{slope of calibration curve})} - 1$$

The carrier used in the amplification efficiency calculation process may have the same form as the carrier used in the extraction efficiency calculation process or may have a different form. For example, in any process, the kind of the cell A and the kind of the nucleic acid, where the cell A and the nucleic acid are included in the carrier, are the same, and in the extraction efficiency calculation process, a carrier whose supporting part is made of a water-decomposable material may be used, and in the amplification efficiency calculation process, a carrier in the form of a plate on which cells are supported may be used.

Further, regarding the carrier used in the amplification efficiency calculation process, it is preferable to use a carrier in which the specific copy number of the nucleic acid present on the base material is the same as the copy number of the detection target gene, or one or more carriers in which the specific copy number of the nucleic acid present on the base material is equal to or larger than the copy number of the detection target gene. Further, for preparing a more accurate calibration curve, it is preferable to use two or more carriers in which the total copy numbers of nucleic acids contained in the carrier (the specific copy number of the nucleic acid present on the base material) are different from each other. It is more preferable to use a carrier in which the specific copy number of the nucleic acid present on the base material is the same as the copy number of the detection target gene, or one or more kinds of carriers in which the specific copy number of the nucleic acid present on the base material is equal to or larger than the copy number of the detection target gene and a carrier in which the specific copy number of the nucleic acid present on the base material is smaller than the copy number of the detection target gene. Further, it is particularly preferable to use two or more carriers in which the specific copy number of the nucleic acid present on the base material is equal to or larger than the copy number of the detection target gene, and one or more carriers in which the specific copy number of the nucleic acid present on the base material is smaller than the copy number of the detection target gene. In the case where a carrier in which the copy number of the nucleic acid present on the base material satisfies the above condition is used, a more accurate calibration curve can be created, and a more accurate amplification efficiency can be calculated. Regarding the "copy number of the detection target gene" referred to herein, the estimated value thereof can be obtained by performing the gene quantification process described later, and the value of the specific copy number of the nucleic acid present on the base material can be set based on the value.

[Gene Quantification Process]

The gene quantification process can be performed in parallel with or before the extraction efficiency calculation process and the amplification efficiency calculation process, and is preferably performed in parallel with the extraction efficiency calculation process and the amplification efficiency calculation process.

In the gene quantification process, a detection target gene is extracted from a cell sample, and quantitative PCR is performed using the extracted gene. The method for extracting an extraction target gene from a cell sample is the same as the method exemplified in the "extraction efficiency calculation process" described above. Further, examples of the quantitative PCR include the same apparatus as that exemplified in the section of <Carrier> described above. The conditions for the quantitative PCR can be appropriately set depending on the gene to be amplified.

[Determination Process B]

In the determination process B, the accuracy of a quantification value of a detection target gene, where the quantification value is obtained from a quantitative PCR apparatus, is determined from the extraction efficiency calculated in the extraction efficiency calculation process and the amplification efficiency calculated in the amplification efficiency calculation process. Specifically, in the case where each of the extraction efficiency and amplification efficiency of the nucleic acid in the carrier, where the nucleic acid is used as an internal standard, is 80% or more, preferably 85% or more, more preferably 90% or more, still more preferably 95% or more, particularly preferably 99% or more, and most preferably 100%, it is determined that the quantification value of the detection target gene by the quantitative PCR apparatus may be accurate. On the other hand, in the case where each of the extraction efficiency and amplification efficiency of the nucleic acid in the carrier, where the nucleic acid is used as an internal standard, is less than 80%, it is determined that the quantification value of the detection target gene by the quantitative PCR apparatus may be inaccurate.

Further, in the determination process, in the case where the extraction efficiency and the amplification efficiency of the gene in the carrier, where the nucleic acid is used as an internal standard, is used as the extraction efficiency and amplification efficiency of the detection target gene, the absolute number of the copy number of the detection target gene contained in the cell sample can be estimated.

EXAMPLES

The present invention will be described with reference to Examples, but the present invention is not limited to Examples below.

Example 1

(Confirmation Test for Extraction Efficiency of Nucleic Acid from Water-Decomposable Carrier)

1. Preparation of Sample

A sample was prepared by applying 500 yeast cells containing one copy of a nucleic acid (6203-a-G (GenBank accession number: AB610938.1)) on a water-decomposable carrier (trade name "120MDP", manufactured by Nippon. Paper Papylia Co., Ltd.,) using inkjet technique.

2. Nucleic Acid Extraction

Then, 0.4 U/4 µL of a yeast cell wall digesting enzyme (trade name "Zymolyase-100T", manufactured by Nacalai Tesque, Inc.) was added dropwise onto a base material made of a water-decomposable material and incubated at 37° C. for 30 minutes. After incubation, a portion at which cells were supported was cut out to a diameter of 6 mm with a biopsy trepan. The cut-out water-decomposable carrier was inserted in a 1.5 mL microtube with forceps, 150 µL of UltraPure Distilled Water (manufactured by Thermo Fisher Scientific, Inc.) was added thereto, and the resultant mixture was vortexed to disperse the nucleic acid in the solution. Then, it was heat treatment was performed at 95° C. for 60 minutes.

3. Nucleic Acid Detection

A nucleic acid was amplified using a real-time PCR apparatus, Quant Studio 7 Flex (manufactured by Thermo Fisher Scientific, Inc.), The composition of the reaction solution for the real-time PCR is shown below.

(Composition of Reaction Solution)

GenCheck qPCR Probe Master (dUTP) (manufactured by Fasmac Co., Ltd.): 25 µL;
100 µM Forward Primer (SEQ ID NO: 1: 5'-TCGAAGGGTGATTGGATCGG-3'): 0.25 µL;
100 µM Reverse Primer (SEQ ID NO: 2: 5'-TGGCTAGCTAAGTGCCATCC-3'): 0.25 µL;
100 µM Prob (SEQ ID NO: 3: FAM-TGCAT-TCTGCCTTCGATTGTCCCTAC-TAMRA): 0.10 µL;
UltraPure Distilled Water (manufactured by Thermo Fisher Scientific, Inc.) 6.4 µL; and
A nucleic acid-containing solution prepared in "2." (theoretical copy number of nucleic acid in solution: 60 copies): 18 µL.

Figure 23:
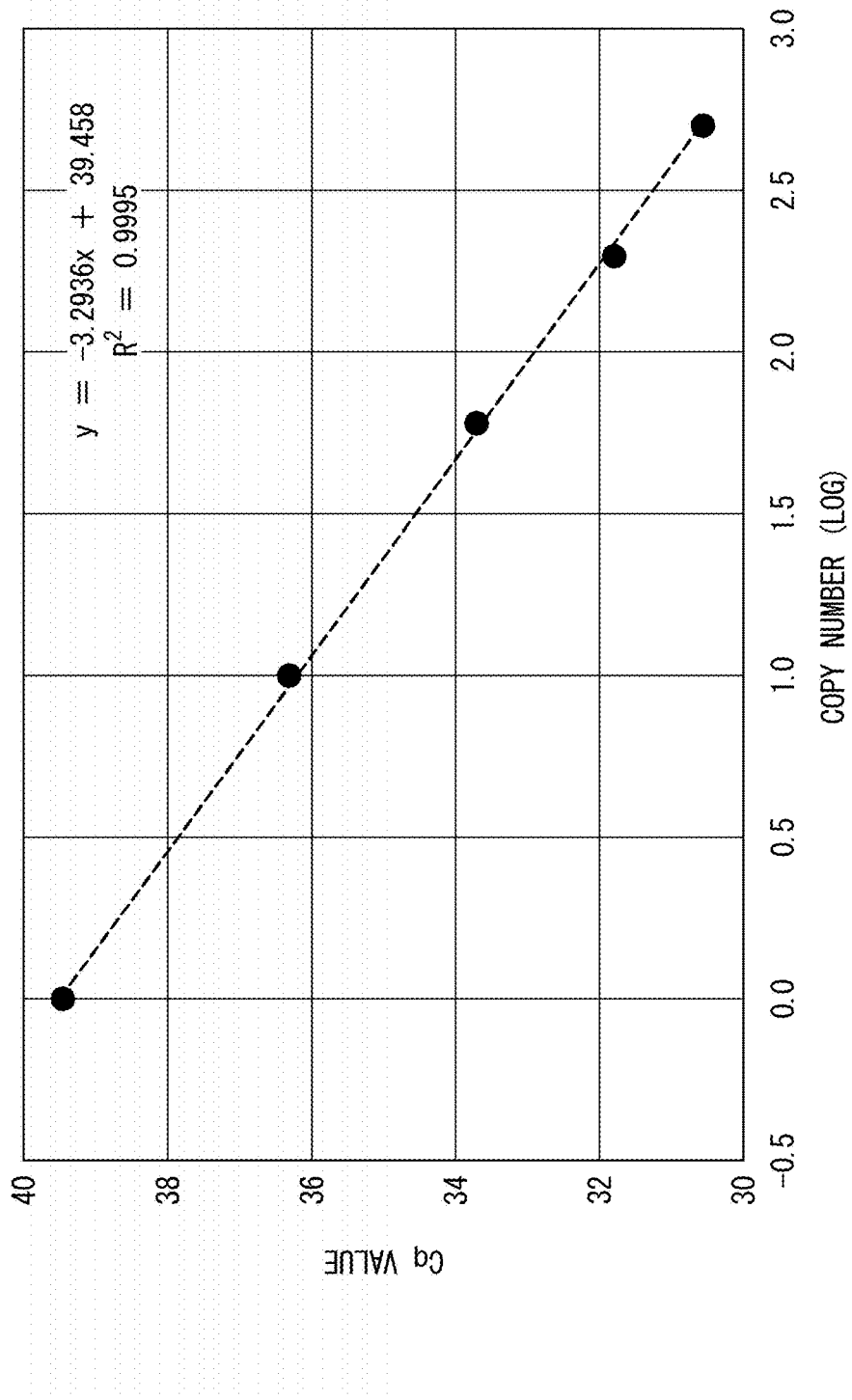
FIG. 23 is a graph showing a calibration curve in Example 1.

PCR was carried out using a reaction solution having the above composition under the reaction conditions shown in Table 2. For quantifying the copy number, a sample was prepared by directly dispensing, with inkjet technique, 1, 10, 60, 200, or 500 cells of the yeast cell containing one copy of a nucleic acid (6203-a-G (GenBank accession number: A13610938.1)) in a 96-well plate for PCR (trade name "MicroAmp Optical 96-Well Reaction Plate, manufactured by Thermo Fisher Scientific, Inc.", this sample was also subjected to the treatment with 0.4 U/4 µL. of a yeast cell wall digesting enzyme, and then amplified by PCR at the same time together with the above sample. The detection results are shown in Table 3. In Table 3, "Extracted nucleic acid" shows the result obtained by performing the same test three times independently. In addition, "Quantitative copy number" is a value calculated from a Cq value by using a calibration curve of the Cq value (see FIG. 23) and the copy number in the real-time PCR which has been performed by using the sample prepared by directly dispensing, with inkjet technique shown in the figure, 1, 10, 60, 200, or 500 cells of the yeast cell containing one copy of a nucleic acid in a 96-well plate. The extraction efficiency is the value obtained by dividing the quantitative copy number by the theoretical copy number.

TABLE 2

| Step | Temp | Time | Cycle |
| --- | --- | --- | --- |
| Polymerase Activation | 50° C. 95° C. | 2 min 10 min | 1 |
| Denaturation | 95° C. | 30 Sec | 50 |
| Annealing/Extension | 61° C. | 1 min | |

TABLE 3

| Condition | Control | | | | | Extracted nuclei acid | | |
| --- | --- | --- | --- | --- | --- | --- | --- | --- |
| Copy number | 1 | 10 | 60 | 200 | 500 | 60 | 60 | 60 |
| Cq value | 39.38 | 36.26 | 33.67 | 31.81 | 30.55 | 33.88 | 33.92 | 33.64 |
| Quantified copy number | | | | | | 49 | 48 | 59 |
| Extraction efficiency | | | | | | 82.1% | 80.0% | 97.6% |

As shown in Table 3, it has been confirmed that the extraction efficiency of the nucleic acid is about 80% or more and 97.6% or less in the case where a water-decomposable carrier on which cells containing a nucleic acid is supported is used.

Example 2

(Confirmation Test for Extraction Efficiency of Nucleic Acid Under Different Yeast Cell Wall Digesting Enzyme Treatment Conditions)

1. Preparation of Sample

A sample was prepared by dispensing, with inkjet technique, 10, 50, or 100 cells of the yeast cell containing one copy of a nucleic acid (6203-a-G (GenBank accession number: AB610938.1)) in a 96-well plate (trade name "MicroAmp Optical 96-Well Reaction Plate, manufactured by Thermo Fisher Scientific, Inc.".

2. Nucleic Acid Extraction

Then, the yeast cell wall digesting enzyme (trade name "Zymolyase-100T", manufactured by Nacalai Tesque, Inc.) was added thereto at each of the concentrations shown in Table 4. A dilution series of the yeast cell wall digesting enzyme were made prepared using a ColE1 ½ TE solution. The ColE1 ½ TE solution was prepared by mixing equal volumes of Tris-EDTA (TE) solution and Distilled Water and adding thereto ColE1 DNA to a concentration of 6 ng/µL. The digestion of the yeast cell wall was performed by incubation at 37° C. for 30 minutes. The enzyme was then deactivated by incubation at 95° C. for 2 minutes. In Table 3, "Negative" is an abbreviation for the negative control and is a sample containing no yeast cells.

TABLE 4

| Condition | Sample copy number | Zymolyase concentration (U/4 µL) |
| --- | --- | --- |
| 1 | Negative | Absent |
| 2 | Negative | 0.4 |
| 3 | 1, 5, 10, 25, 50, 100 (calibration curve) | 0.4 |
| 4 | 10, 50, 100 | 0.4 |
| 5 | 10, 50, 100 | 0.04 |
| 6 | 10, 50, 100 | 0.004 |
| 7 | 10, 50, 100 | 0.0004 |
| 8 | 10, 50, 100 | 0.00004 |
| 9 | 10, 50, 100 | 0.000004 |
| 10 | 10, 50, 100 | 0.0000004 |

3. Nucleic Acid Detection

PCR was carried out under the reaction conditions shown in Table 1 above, using a reaction solution having the same composition as that of Example 1 except that 4 µL of the nucleic acid-containing solution prepared in "2." was used. In the PCR, a sample was prepared by dispensing, with inkjet technique, 1, 5, 10, 25, 50, or 100 cells in a 96-well plate (trade name "MicroAmp Optical 96-Well Reaction Plate, manufactured by Thermo Fisher Scientific, Inc." and amplified at the same time together with the enzyme-treated sample (Condition 3 in Table 4 above), thereby obtaining a calibration curve. This calibration curve was used to apply 10, 50, or 100 cells, and the copy number of the nucleic acid in the samples having different cell concentration was quantified. In addition, the extraction efficiency of the nucleic acid for each enzyme concentration was calculated by dividing the quantified copy number by the theoretical copy number (10, 50, or 100 copies). The results are shown in Table 5. In Table 5, "UD number" is the number of wells in which the nucleic acid was not amplified. In addition, a graph showing the change in the extraction efficiency of the nucleic acid due to the difference in enzyme concentration for each copy number is shown in FIG. 24, and a graph showing the change in the calibration curve that has been created using samples of 10, 50 and 100 copies due to the difference in enzyme concentration is shown in FIG. 25.

TABLE 5

| Copy number | Zymolyase [U] | 4.0E−01 | 4.0E−02 | 4.0E−03 | 4.08−04 | 4.0E−05 | 4.0E−06 | 4.0E−07 |
|---|---|---|---|---|---|---|---|---|
| 10 | Cq ave. | 33.63 | 33.72 | 35.58 | 37.10 | 39.39 | 36.72 | — |
|  | UD number | 0 | 0 | 0 | 0 | 0 | 1 | 3 |
|  | Copy number | 10 | 7.8 | 2.2 | 0.7 | 0.1 | 1.1 | 0 |
|  | Efficiency | 100% | 78.0% | 22.2% | 6.8% | 1.3% | 11.1% | 0% |
| 50 | Cq ave. | 31.17 | 31.35 | 32.85 | 35.47 | 39.63 | 36.86 | 40.55 |
|  | UD number | 0 | 0 | 0 | 0 | 0 | 2 | 1 |
|  | Copy number | 50 | 44.5 | 14.8 | 2.8 | 0.2 | 0.8 | 0.5 |
|  | Efficiency | 100% | 88.9% | 29.5% | 5.6% | 0.3% | 1.6% | 1.0% |
| 100 | Cq ave. | 30.22 | 30.22 | 31.91 | 34.24 | 36.75 | 36.83 | 36.50 |
|  | UD number | 0 | 0 | 0 | 0 | 0 | 1 | 1 |
|  | Copy number | 100 | 101.4 | 29.6 | 5.7 | 1.0 | 0.8 | 1.2 |
|  | Efficiency | 100% | 101% | 29.6% | 5.7% | 1.0% | 0.8% | 1.2% |

Figure 24:
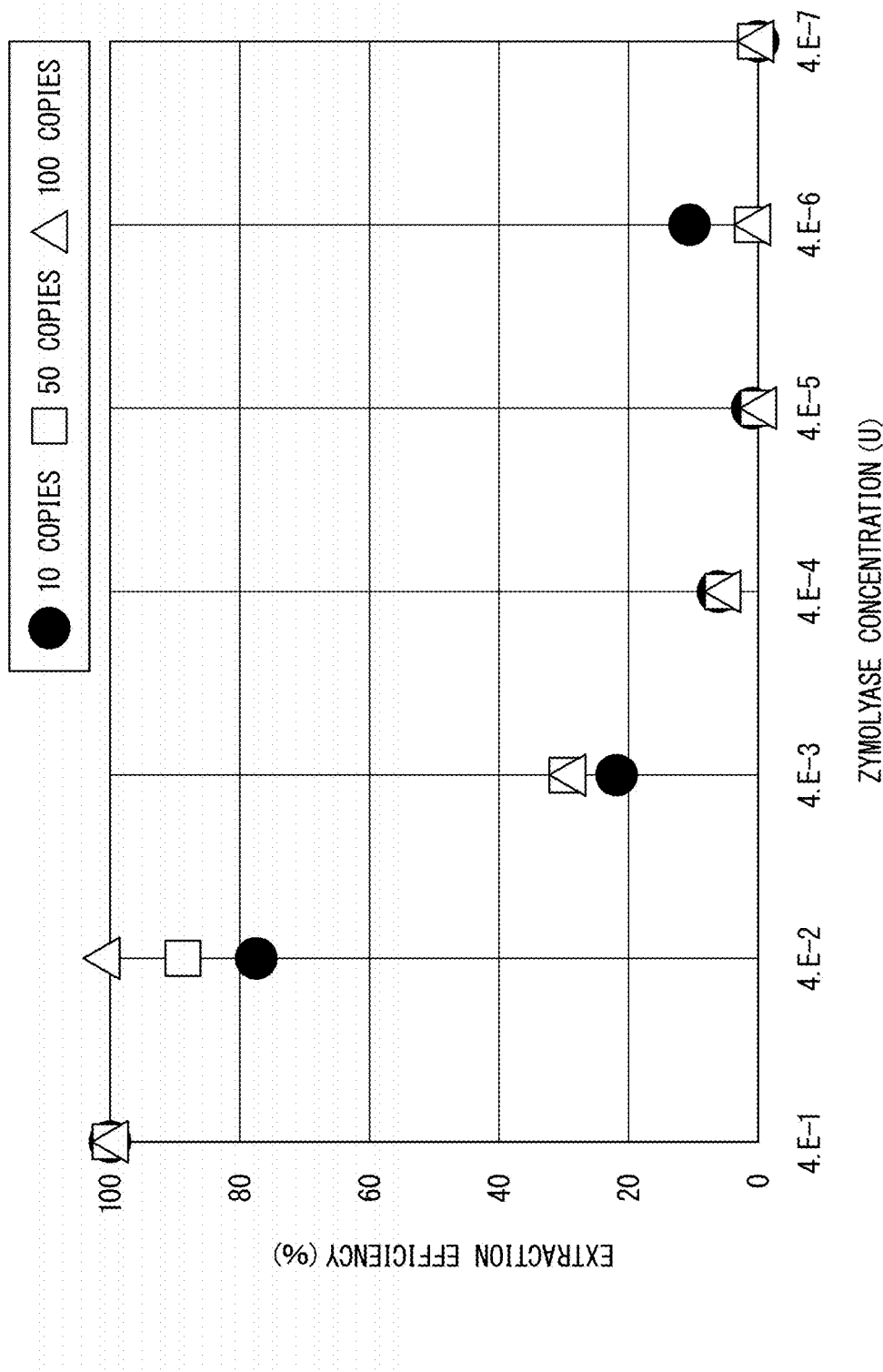
FIG. 24 is a graph showing changes in the extraction efficiency of the nucleic acid due to a difference in enzyme concentration for each copy number in Example 2.
Figure 25:
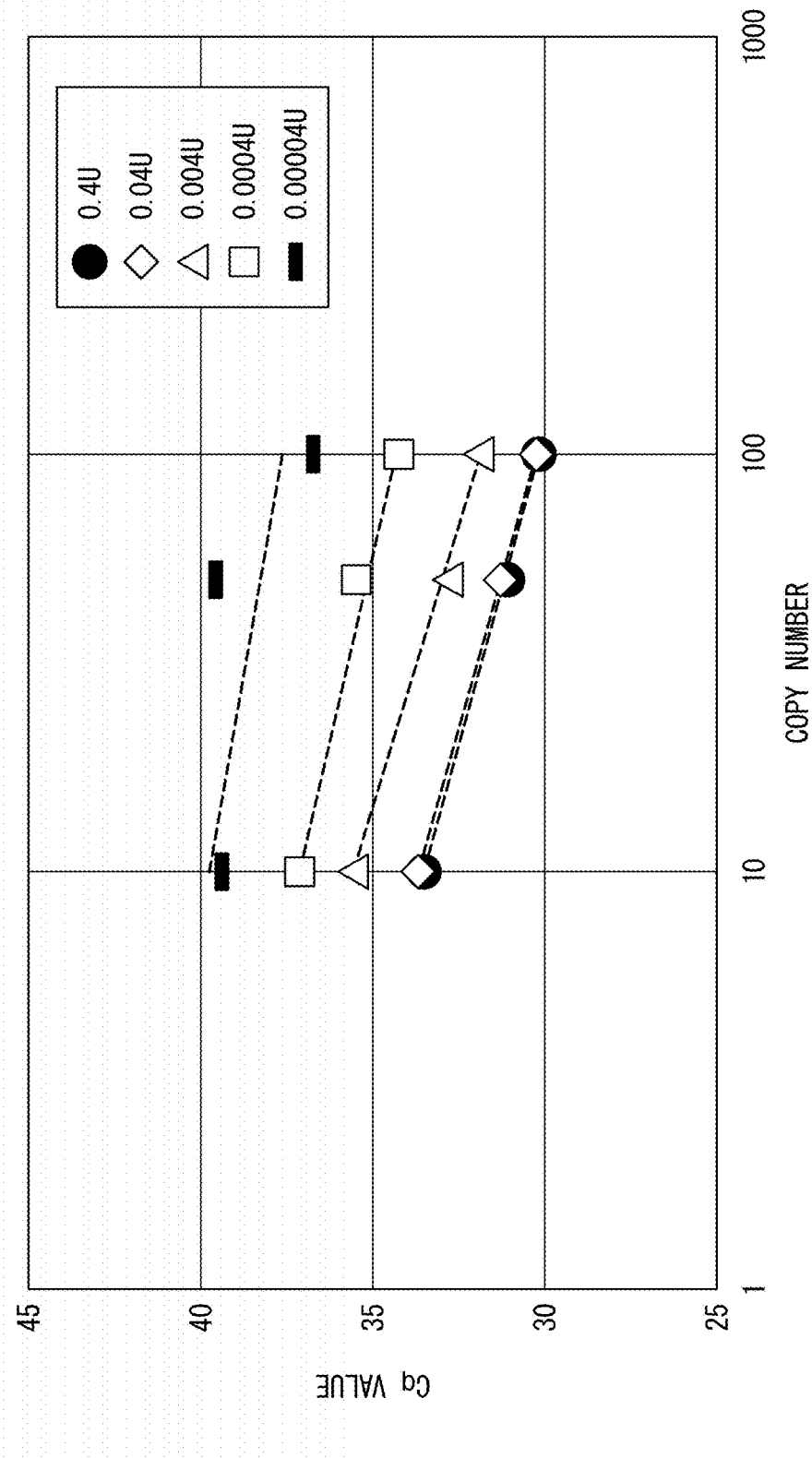
FIG. 25 is a graph showing changes due to differences in enzyme concentrations of a calibration curve created using samples of 10, 50, and 100 copies in Example 2.

From Table 5, FIG. 24, and FIG. 25, it has been confirmed that in samples containing 10 or 50 copies of nucleic acid, the extraction efficiency of the nucleic acid tends to decrease as the enzyme concentration decreases. In the sample containing 100 copies of nucleic acid, the decrease in extraction efficiency of nucleic acid due to the decrease in enzyme concentration was remarkable at the enzyme concentration of 0.004 U/4 μL or less.

In all samples having any copy number, it has been confirmed that the extraction efficiency of nucleic acid tends to decrease due to the decrease in enzyme concentration.

The present invention includes the following aspects.

(1) A carrier which is a carrier for testing the accuracy of a measurement value of a detection target gene in a cell sample, the measurement value being obtained from a genetic testing apparatus, including a supporting part on which a specific number of cells A are supported, in which the cells A contain a specific number of copies of a nucleic acid, and the supporting part is made of a water-decomposable material.

(2) The carrier according to (1), in which the nucleic acid is incorporated into a nucleic acid in a nucleus of the cells A.

(3) The carrier according to (1) or (2), in which the copy number of the nucleic acid is one.

(4) The carrier according to (3), in which the number of cells A is 1 or more and 500 or less.

(5) The carrier according to any one of (1) to (4), in which the carrier is a carrier for testing the accuracy of a measurement value of a detection target gene in a cell sample, the measurement value being obtained from a genetic testing apparatus.

(6) The carrier according to (5), in which the nucleic acid and the gene have sequences different from each other.

(7) The carrier according to (5) or (6), in which the cells A and the cell containing the gene are derived from the same species and are the same kind cell.

(8) The carrier according to any one of (5) to (7), in which the genetic testing apparatus is a quantitative PCR apparatus.

(9) A method for testing the accuracy of a measurement value of a detection target gene in a cell sample, the measurement value being obtained from a genetic testing apparatus, including using a carrier including a supporting part on which a specific number of cells A are supported, the cells A containing a specific number of copies of a nucleic acid.

(10) The method according to (9), in which the supporting part is made of a water-decomposable material.

(11) The method according to (9) or (10), further including: calculating the extraction efficiency of the nucleic acid from the cells A using the carrier.

(12) The method according to any one of (9) or (10), in which the genetic testing apparatus is a quantitative PCR apparatus.

(13) The method according to (12), further including: calculating the extraction efficiency of the nucleic acid from the cells A using the carrier, using the carrier to amplify the nucleic acid by the quantitative PCR apparatus and creating a calibration curve to calculate the amplification efficiency, and determining the accuracy of a quantification value of the gene from the extraction efficiency, the amplification efficiency, and the quantification value obtained from the quantitative PCR apparatus.

While preferred embodiments of the invention have been described and shown above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

EXPLANATION OF REFERENCES

1: Carrier
2: Supporting part
3: Cell A
4: Nucleic acid
5: Base material
10, 10', 10C: Ejection head (liquid droplet-ejecting means)
11, 11a, 11b, 11c, 11C, 11': Liquid chamber
12, 12C: Membrane
13, 13C: Driving element
13a: Electric motor 13b, 13c: Piezoelectric element
20: Driving means
30, 260: Light source
40: Mirror
60, 61: Light-receiving element
70: Controlling means
71, 101: CPU
72: ROM
73: RAM
74, 106: OF
75: Bus line
100: Performance evaluation device
102: Main storage device
103: Auxiliary storage device
104: Output device
105: Input device
107: Bus
111, 111a, 111b, 111c, 121: Nozzle
112: Solenoid valve
115: Atmospheric air opening part
200: Coil
250: Micro flow path
255: Detector
255': Image acquisition part
265.265': Lens
300, 300a, 300b, 300c: Ce 'suspension
310, 310': Liquid droplet
350, 350a, 350b, 350', 350": Cell
400: Dispensing device
401, 401A, 401B, 401C: Liquid droplet-forming device
700, 700': Base material
710: Supporting part
800: Stage
900: Control device
L: Light
Lf, Lf$_1$, Lf$_2$: Fluorescence
[Patent Document 1] Japanese Patent No, 5875230

What is claimed is:

1. A carrier, comprising:
a supporting part on which a specific number of cells A are supported,
wherein the cells A contain a specific number of copies of a nucleic acid, wherein the number of cells A is known, and the copy number of the nucleic acid is known,
wherein the supporting part is made of a water-decomposable material, and
wherein the number of cells A is 1 or more and 500 or less.

2. The carrier according to claim 1, wherein the nucleic acid is incorporated into a nucleic acid in a nucleus of the cells A.

3. The carrier according to claim 1, wherein the copy number of the nucleic acid is one.

4. The carrier according to claim 1, wherein the carrier is a carrier suitable for testing the accuracy of a measurement value of a detection target gene in a cell sample, the measurement value being obtained from a genetic testing apparatus.

5. The carrier according to claim 4, wherein the nucleic acid and the gene have sequences different from each other.

6. The carrier according to claim 4, wherein the cells A and the cell containing the gene are derived from the same species and are the same kind of cell.

7. The carrier according to claim 4, wherein the genetic testing apparatus is a quantitative PCR apparatus.

8. A method for testing the accuracy of a measurement value of a detection target gene in a cell sample, the measurement value being obtained from a genetic testing apparatus, the method comprising:
employing a carrier including a supporting part on which a specific number of cells A are supported, the cells A containing a specific number of copies of a nucleic acid,
wherein the number of cells A is known, and the copy number of the nucleic acid is known,
wherein the number of cells A is 1 or more and 500 or less, to thereby test the accuracy of the measurement value of the detection target gene in the cell sample.

9. The method according to claim 8, wherein the supporting part is made of a water-decomposable material.

10. The method according to claim 8, further comprising:
calculating the extraction efficiency of the nucleic acid from the cells A using the carrier.

11. The method according to claim 8, wherein the genetic testing apparatus is a quantitative PCR apparatus.

12. The method according to claim 11, further comprising:
calculating the extraction efficiency of the nucleic acid from the cells A using the carrier;
using the carrier to amplify the nucleic acid by the quantitative PCR apparatus and creating a calibration curve to calculate the amplification efficiency; and
determining the accuracy of a quantification value of the gene from the extraction efficiency, the amplification efficiency, and the quantification value obtained from the quantitative PCR apparatus.

13. The carrier according to claim 1, wherein the cells (A) are indirectly attached to the support part.

14. The carrier according to claim 1, wherein the cells (A) are directly attached to the support part.

15. The method according to claim 8, wherein the cells (A) are indirectly attached to the support part.

16. The method according to claim 8, wherein the cells (A) are directly attached to the support part.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 1
tcgaagggtg attggatcgg                                            20

<210> SEQ ID NO 2
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 2
tggctagcta agtgccatcc                                            20

<210> SEQ ID NO 3
<211> LENGTH: 26
<212> TYPE: DNA
<213> ORGANISM: Artificial Sequence
<220> FEATURE:
<223> OTHER INFORMATION: Synthesized oligonucleotide

<400> SEQUENCE: 3
tgcattctgg cttcgattgt ccctac                                     26